United States Patent
Tomita et al.

(10) Patent No.: US 11,397,185 B2
(45) Date of Patent: Jul. 26, 2022

(54) METHOD FOR ANALYZING PROTEIN-CONTAINING SAMPLE

(71) Applicant: NATIONAL INSTITUTE OF ADVANCED INDUSTRIAL SCIENCE AND TECHNOLOGY, Tokyo (JP)

(72) Inventors: Shunsuke Tomita, Ibaraki (JP); Sayaka Ishihara, Ibaraki (JP); Ryoji Kurita, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 522 days.

(21) Appl. No.: 16/348,312

(22) PCT Filed: Nov. 10, 2017

(86) PCT No.: PCT/JP2017/040542
§ 371 (c)(1),
(2) Date: May 8, 2019

(87) PCT Pub. No.: WO2018/088510
PCT Pub. Date: May 17, 2018

(65) Prior Publication Data
US 2019/0265249 A1 Aug. 29, 2019

(30) Foreign Application Priority Data
Nov. 11, 2016 (JP) .............................. JP2016-220548

(51) Int. Cl.
*G01N 33/68* (2006.01)
*G01N 33/58* (2006.01)
(Continued)

(52) U.S. Cl.
CPC ............ *G01N 33/6803* (2013.01); *C09K 9/02* (2013.01); *C09K 11/06* (2013.01); *G01N 21/64* (2013.01);
(Continued)

(58) Field of Classification Search
CPC ...... C09K 9/02; C09K 11/06; G01N 33/6803; G01N 33/582; G01N 2440/00; G01N 21/64; G01N 33/483
See application file for complete search history.

(56) References Cited

U.S. PATENT DOCUMENTS 5,583,195 A 12/1996 Eckberg
8,021,891 B2 9/2011 Rotello et al.
(Continued)

FOREIGN PATENT DOCUMENTS

JP 09-183853 7/1997
JP 2007060953 A 3/2007
(Continued)

OTHER PUBLICATIONS

De et al. "Sensing of proteins in human serum using conjugates of nanoparticles and green fluorescent protein" Nature Chemistry, 1:461-465 (2009).
(Continued)

*Primary Examiner* — Rebecca M Fritchman
(74) *Attorney, Agent, or Firm* — Myers Bigel, P.A.

(57) ABSTRACT

Provided is a method for analyzing a protein-containing sample. The method comprises (1) dissolving a probe capable of non-specifically interacting with a plurality of proteins in a plurality of solvents having different ionic strengths and/or pH levels; (2) adding a protein-containing sample to a plurality of probe solutions prepared in the step (1), thereby the proteins in the sample and the probe are interacted non-specifically; (3) measuring the fluorescence
(Continued)

intensities of the plurality of probe solutions to which the protein-containing sample was added in the step (2); and (4) comparing the pattern of fluorescence intensities obtained in the step (3) with the pattern of fluorescence intensities obtained from a reference sample.

12 Claims, 28 Drawing Sheets

(51) Int. Cl.
    *C09K 9/02*     (2006.01)
    *C09K 11/06*     (2006.01)
    *G01N 21/64*     (2006.01)
    *G01N 33/483*     (2006.01)

(52) U.S. Cl.
    CPC ......... *G01N 33/483* (2013.01); *G01N 33/582* (2013.01); *G01N 2440/00* (2013.01)

(56) References Cited

U.S. PATENT DOCUMENTS

| | | | |
|---|---|---|---|
| 2009/0221099 A1* | 9/2009 | Rotello | G01N 33/54313 436/501 |
| 2011/0177976 A1 | 7/2011 | Gordon et al. | |
| 2014/0357503 A1* | 12/2014 | Hof | C07C 309/60 506/7 |
| 2016/0349245 A1 | 12/2016 | Zhang et al. | |
| 2019/0331693 A1 | 10/2019 | Figeys et al. | |

FOREIGN PATENT DOCUMENTS

| | | |
|---|---|---|
| JP | 2012132753 A | 7/2012 |
| JP | 2016106632 A | 6/2016 |
| WO | 2017205981 A1 | 12/2017 |

OTHER PUBLICATIONS

English Translation of International Search Report corresponding to International Patent Application No. PCT/JP2017/040542 (2 pages) (dated Feb. 6, 2018).

Minaker et al. "Antibody-Free Reading of the Histone Code Using a Simple Chemical Sensor Array" Journal of the American Chemical Society, 134:11674-11680 (2012).
Tomita et al. "Artificial Modification of an Enzyme for Construction of Cross-Reactive Polyion Complexes To Fingerprint Signatures of Proteins and Mammalian Cells" Analytical Chemistry, 88:9079-9086 (2016).
Tomita et al. "The Use of an Enzyme-based Sensor Array to Fingerprint Proteomic Signatures of Sera from Different Mammalian Species" Analytical Sciences, 32:237-240 (2016).
Tomita et al. "Environment-Sensitive Turn-On Fluorescent Polyamino Acid: Fingerprinting Protein Populations with Post-Translational Modifications" Applied Materials & Interfaces, 9:22970-22976 (2017).
You et al. "Detection and identification of proteins using nanoparticle-fluorescent polymer 'chemical noise' sensors" Nature Nanotechnology, 2:318-323 (2007).
Zamora-Olivares et al. "In-Situ Generation of Differential Sensors that Fingerprint Kinases and the Cellular Response to Their Expression" Journal of the American Chemical Society, 135:14814-14820 (2013).
Benjdia et al. "Post-translational modification of ribosomally synthesized peptides by a radical SAM epimerase in Bacillus subtilis" Nature Chemistry, 9(7):698-707 (2017).
Costea et al. "Enterotypes in the landscape of gut microbial community composition" Nature Microbiology, 3:8-16 (2018).
Gately, Stephen "Human Microbiota and Personalized Cancer Treatments: Role of Commensal Microbes in Treatment Outcomes for Cancer Patients" Cancer Treatment & Research, Chapter 10, pp. 253-264 (2019).
Gilbert et al. "Microbiome-wide association studies link dynamic microbial consortia to disease" Nature, 535:94-103 (2016).
Hogmander et al. "Luminometric Label Array for Counting and Differentiation of Bacteria" Analytical Chemistry, 89:3208-3216 (2017).
Ji et al. "Point-of-Care Identification of Bacteria Using Protein-Encapsulated Gold Nanoclusters" Advanced Healthcare Materials, 7:1701370 (6 pages) (2018).
Lai et al. "Metaproteomics Study of the Gut Microbiome" Methods in Molecular Biology, Chapter 8, 1871:123-132 (2019).

* cited by examiner

FIG.1
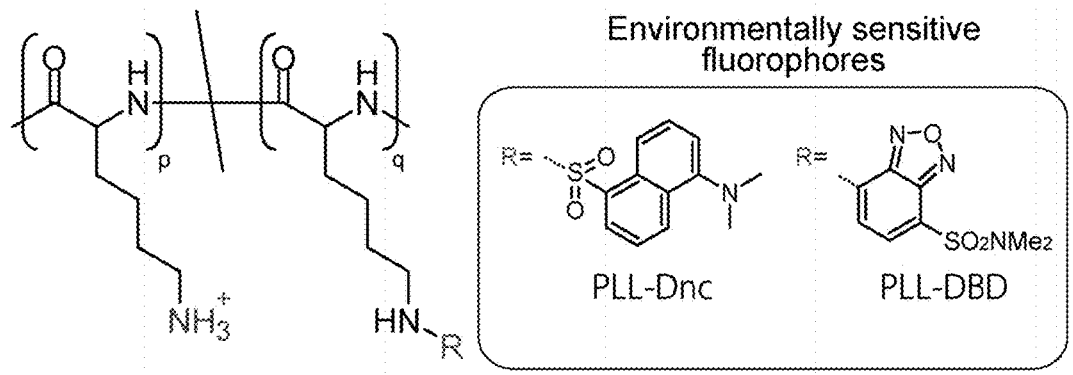
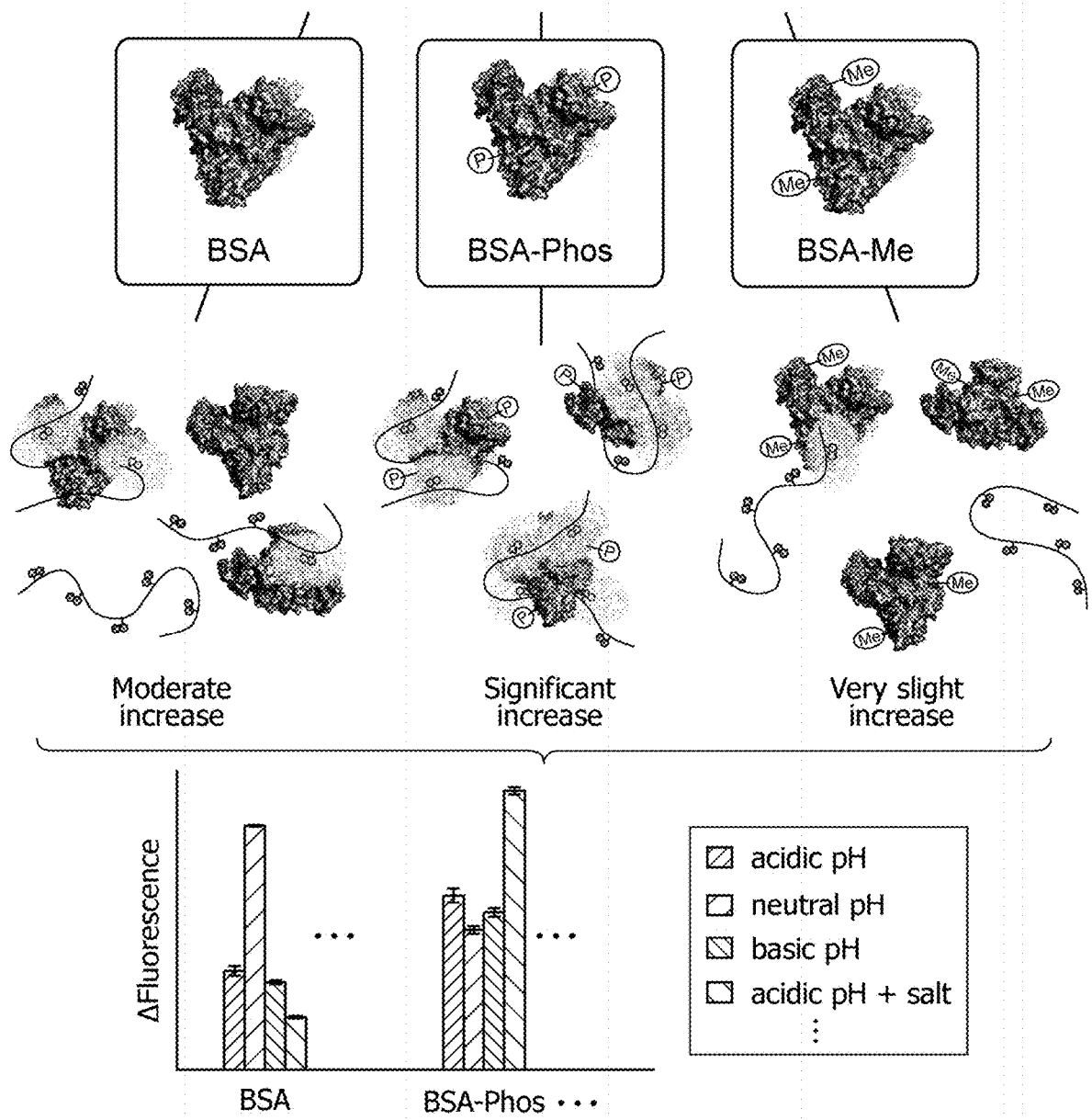

Environmentally sensitive fluorophores

PLL-Dnc (n=4.4)
PLL-DBD (n=4.6)

Poly-L-Lysine
P1: p = 9, q = 1, (12%)
P2: p = 48, q = 7, (12%)
P3: p = 230, q = 28, (11%)

Poly(ethylene glycol)-block-Poly-(L-Lysine)
P4: p = 46, q = 6 (12%)

G4 PAMAM dendrimer

P5: p = 56, q = 8 (12%)

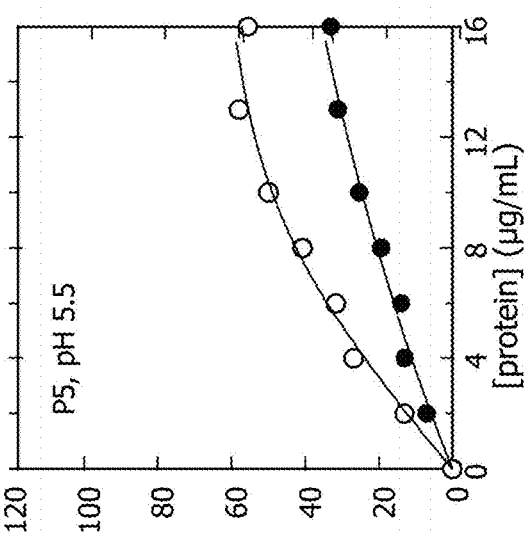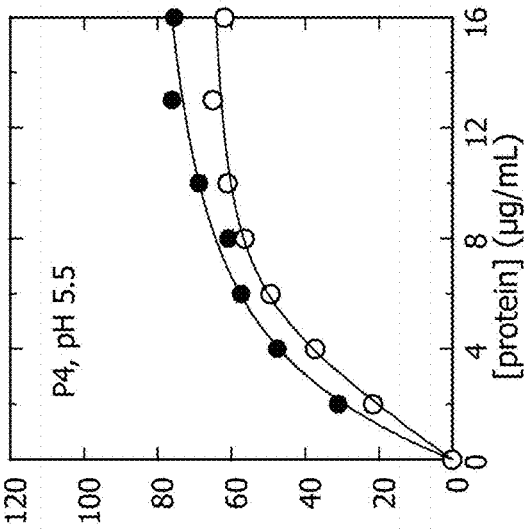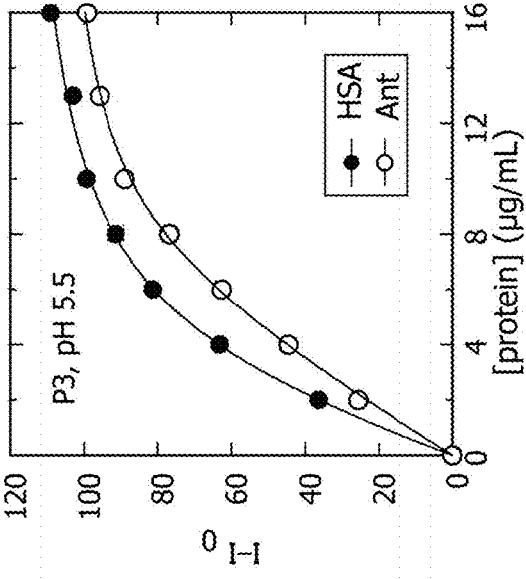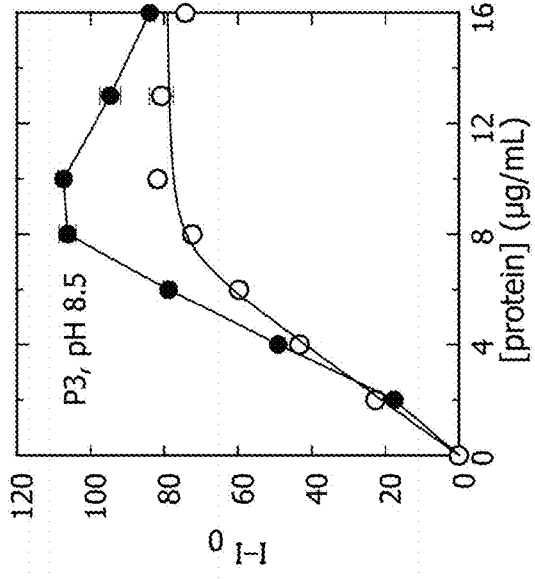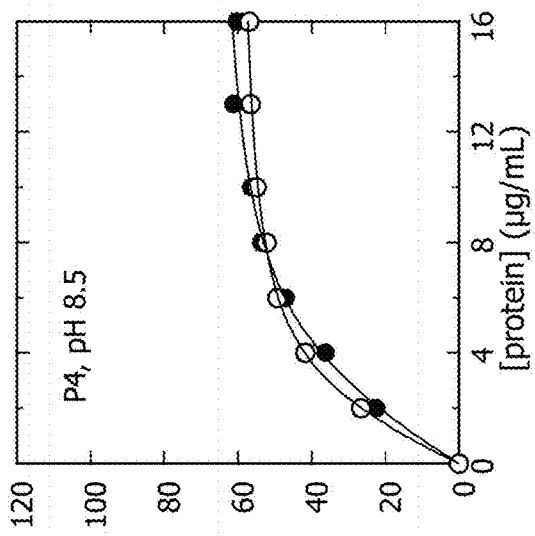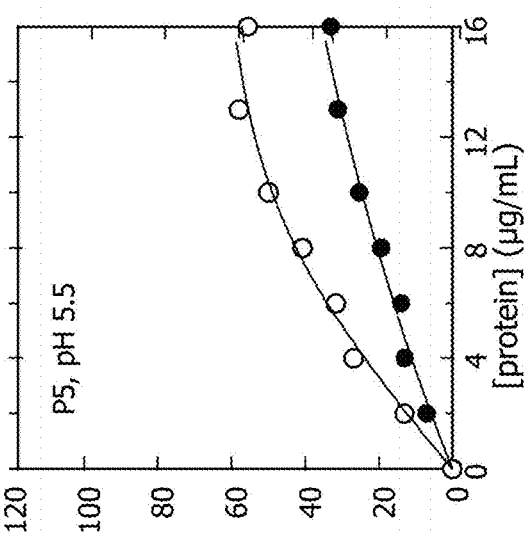

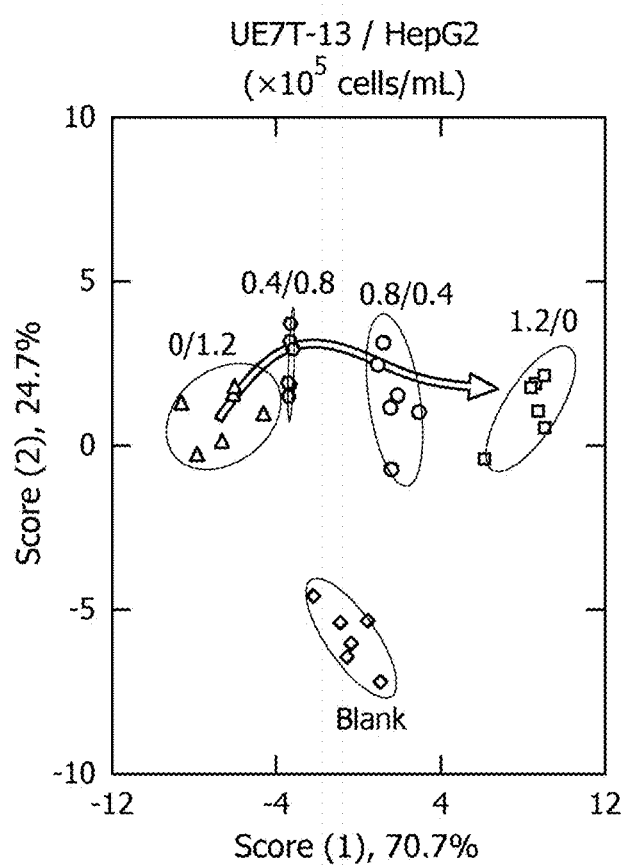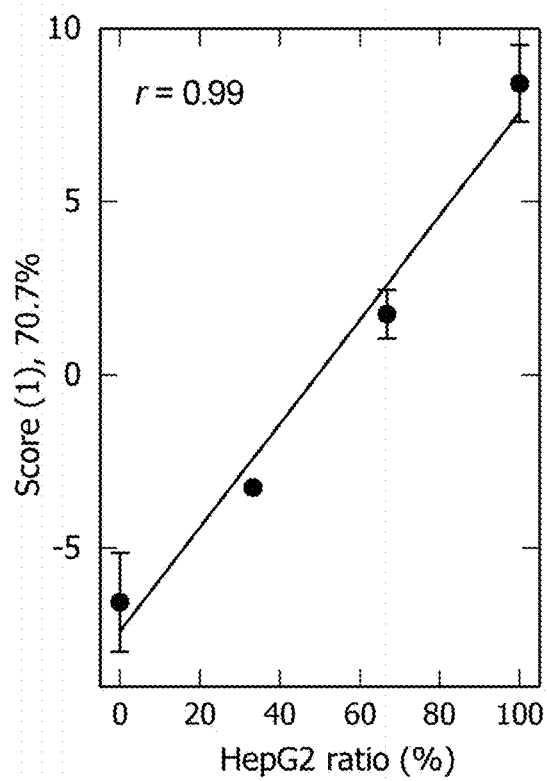
FIG.29A
FIG.29B

METHOD FOR ANALYZING PROTEIN-CONTAINING SAMPLE

TECHNICAL FIELD

The present invention relates to a method for determining types and/or amounts of proteins and post-translational protein modifications, and relates to a method for determining the types and/or states and/or concentrations of cells being cultured.

BACKGROUND ART

Proteins are synthesized in cells by transcription from DNA to mRNA, and by translation from mRNA to polypeptides, and the polypeptides are then subjected to various chemical modifications. These modifications are called post-translational modifications (PTMs), and 300 or more types of PTMs, such as phosphorylation, acetylation, ubiquitination, and saccharification, have been reported. It is also known that one type of PTM, or cross-talk of a number of different types of PTMs, regulates activity, localization, interaction, etc., of proteins so as to control cell function. In addition, in recent years, it is being revealed that abnormalities in PTMs are directly involved in pathogenesis and pathology of various diseases, such as cancer, cardiovascular disease, and autoimmune disease. Accordingly, analysis of PTMs is extremely important not only for elucidation of cell function, but also for elucidation of the pathogenic mechanism and pathology of disease, and further establishment of new diagnostic methods and development of new drugs based on the elucidation.

In order to detect a PTM quickly and easily, an antibody specific for that PTM has been used. Thousands of PTM-specific antibodies have been marketed so far, and various biochemical assays are performed by methods such as Western blotting, flow cytometry, and chromatin immunoprecipitation. However, antibodies are proteins and are therefore unstable, and there is a problem in that the production thereof is time-consuming and expensive. In addition, PTM-specific antibodies must be capable of distinguishing a slight difference, i.e., the presence or absence of a modification in identical proteins, and it is extremely difficult to produce such a high-quality antibody. Furthermore, since most of PTM-specific antibodies are polyclonal antibodies, lot-to-lot variation in quality is also often a problem. In view of these circumstances, a new PTM detecting method is desired that can be easily and inexpensively implemented and that uses a compound having high stability and less lot-to-lot variation.

A method of identifying a protein by cross-reactive sensing is an example of a method that may solve the above-mentioned problems. This method uses molecules cross-reacting with a plurality of proteins contained in a sample as an analytical target, rather than using molecules such as an antibody, specifically interacting with a specific target protein in a sample as an analytical target, and identifies proteins in the sample by statistically analyzing the reaction pattern of the plurality of proteins with the cross-reactive molecules. Accordingly, the cross-reactive sensing does not require developing molecules that specifically interact with a target protein, and has an advantage in that the development is relatively easy.

It was reported by about 2010 that a plurality of proteins of different types can be distinguished by cross-reactive sensing (Patent Document 1, and Non-Patent Documents 1 and 2), but recently it has also been reported that the presence or absence of a PTM in identical proteins can be distinguished. For example, a method for distinguishing the presence or absence of methylation or acetylation at the N-terminal tail histone by using a complex of a p-sulfonatocalix derivative and a fluorescent dye has been reported (Patent Document 2 and Non-Patent Document 3). However, this method utilizes the ability to specifically recognize lysine residues of the p-sulfonatocalix derivative, and it is therefore not suitable for detection of phosphorylation occurring in neutral amino acids, such as serine and tyrosine, and methylation occurring in anionic amino acids, such as glutamic acid and aspartic acid. A method for distinguishing the presence or absence of phosphorylation of protein using a complex of 1,3,5-triacryloylhexahydro-1,3,5-triazine, into which a peptide specifically interacting with the phosphorylation site of protein is introduced, and a fluorescent dye has also been reported (Non-Patent Document 4). However, since this method uses a peptide specifically recognizing a PTM, it is necessary to produce different peptides for each PTM, and it is difficult to apply this method to analysis of a wide variety of PTMs. In addition, in every method mentioned above, since a compound recognizing a PTM and a fluorescent dye for detection are used in combination, construction of the detection system is complicated, and detection sensitivity is also low (4 to 5 µM). Accordingly, analytical accuracy and efficiency are inadequate.

CITATION LIST

Patent Document

Patent Document 1: U.S. Pat. No. 8,021,891 B
Patent Document 2: US 2014/0357503 A

Non-Patent Document

Non-Patent Document 1: You, C. C. et al., Nat. Nanotechnol., Vol. 2, pp. 318-323 (2007)
Non-Patent Document 2: De, M. et al., Nat. Chem., Vol. 1, pp. 461-465 (2009)
Non-Patent Document 3: Minaker, S. A. et al., J. Am. Chem. Soc., Vol. 134, pp. 11674-11680 (2012)
Non-Patent Document 4: Zamora-Olivares, D. et al., J. Am. Chem. Soc., Vol. 135, pp. 14814-14820 (2013)

SUMMARY OF INVENTION

Technical Problem

It is an object of the present invention to provide an analytical method that solves the problems in the prior art and can distinguish not only the type of a protein, but also the presence or absence of a PTM in identical proteins, easily and with high accuracy. It is also an object of the present invention to provide a method for distinguishing the type and/or state and/or concentration of cells being cultured with high accuracy and noninvasively.

Solution to Problem

The present inventors have earnestly researched and, as a result, have succeeded in obtaining a probe that can detect a wide variety of types of PTMs with high sensitivity. Furthermore, the inventors have established a method for distinguishing and quantifying the presence or absence and the type of a PTM in a target protein by using the probe and a method for determining the type and/or state and/or concentration of cells being cultured based on the change in the protein component of a cell culture supernatant.

That is, the present invention provides, according to an embodiment, a probe for distinguishing types and/or amounts of protein and post-translational modifications thereto, wherein the probe comprises (1) a cationic polymer comprising at least five primary amino groups in one molecule and having a weight-average molecular weight of 1,000 to 500,000 and (2) an environment-sensitive fluorophore having a naphthalenesulfonic acid structure or a benzofurazan structure, wherein the fluorophore is covalently bonded to some of the primary amino groups in the cationic polymer.

In addition, the present invention provides, according to an embodiment, an array for distinguishing types and/or amounts of protein and post-translational modification thereto, the array comprising the probe dissolved in a plurality of solvents having different ionic strengths and/or pH levels and disposed in a plurality of separate sections on a substrate.

In addition, the present invention provides, according to an embodiment, a method for analyzing a protein-containing sample, comprising (1) dissolving a probe capable of non-specifically interacting with a plurality of proteins in a plurality of solvents having different ionic strengths and/or pH levels, wherein the probe comprises (a) a cationic polymer comprising at least five primary amino groups in one molecule and having a weight-average molecular weight of 1,000 to 500,000 and (b) an environment-sensitive fluorophore having a naphthalenesulfonic acid structure or a benzofurazan structure, wherein the fluorophore is covalently bonded to some of the primary amino groups in the cationic polymer; (2) adding a test sample comprising one or more proteins to a plurality of probe solutions prepared in the step (1), thereby the proteins in the test sample and the probe are interacted non-specifically; (3) measuring the fluorescence intensities of the plurality of probe solutions to which the test sample has been added in the step (2); and (4) comparing the pattern of fluorescence intensities obtained in the step (3) with the pattern of fluorescence intensities obtained from a reference sample.

The environment-sensitive fluorophore is preferably selected from the group consisting of dansyl, dimethylaminosulfonyl benzoxadiazole, and fluorescent derivatives thereof.

The cationic polymer is preferably a linear or branched polyamino acid, polyallylamine, polyamidoamine, or polyalkyleneimine.

The polyamino acid is preferably polylysine or polyornithine.

The environment-sensitive fluorophore is covalently bonded to preferably 1% to 50% of the primary amino groups in the cationic polymer.

A functional group selected from the group consisting of a guanidium group, an alkyl group, an aryl group, a carboxyl group, and an amino acid may be introduced into at least some of the primary amino groups not covalently bonded to the environment-sensitive fluorophore in the cationic polymer.

The measurement of the fluorescence intensities in the step (3) is preferably performed at a plurality of excitation wavelengths and emission wavelengths.

In the step (4), types and/or amounts of protein and post-translational modification thereto contained in the sample are preferably determined.

The sample is preferably a cell culture supernatant, and in the step (4), the type and/or state and/or concentration of cells being cultured are preferably determined.

The state of the cells being cultured is preferably a degree of cell differentiation.

Advantageous Effects of Invention

The probe according to the present invention can interact with any protein and can detect the presence or absence of various PTMs in a protein of interest with high sensitivity regardless of the sequence of the protein of interest and the sites introduced PTMs.

In addition, a "unique fluorescent fingerprint" can be obtained depending on the type of protein and the state of introduced PTM by using the probe according to the present invention dissolved in a plurality of solvents having different ionic strengths and/or pH levels. Accordingly, the method according to the present invention for distinguishing types and/or amounts of protein and post-translational modification thereto can easily analyze a wide variety of types of proteins and/or PTMs by using only one type of probe molecules.

Furthermore, the type and/or state and/or concentration of cells being cultured can be distinguished with high accuracy and noninvasively by the method of the present invention for analyzing a protein-containing sample by using only one or a few types of probe molecules.

BRIEF DESCRIPTION OF DRAWINGS

FIG. 1 is a schematic diagram illustrating the principle of a method for distinguishing the type and/or amount of a post-translational modification by an embodiment of the present invention.

FIG. 8 shows graphs showing the results of characterization for PLL (number of units: 258)-Dnc (Compound 5: P3), polyethylene glycol-PLL block copolymer-Dnc (Compound 6: P4), and PAMAM dendrimer-Dnc (Compound 7: P5).

FIG. 29 shows graphs obtained by analyzing the results shown in FIG. 26 by linear discriminant analysis and plotting the resulting quadratic discriminant scores (a) and plotting the ratios of HepG2 with respect to the resulting linear discriminant scores (b).

DESCRIPTION OF EMBODIMENTS

Figure 2:
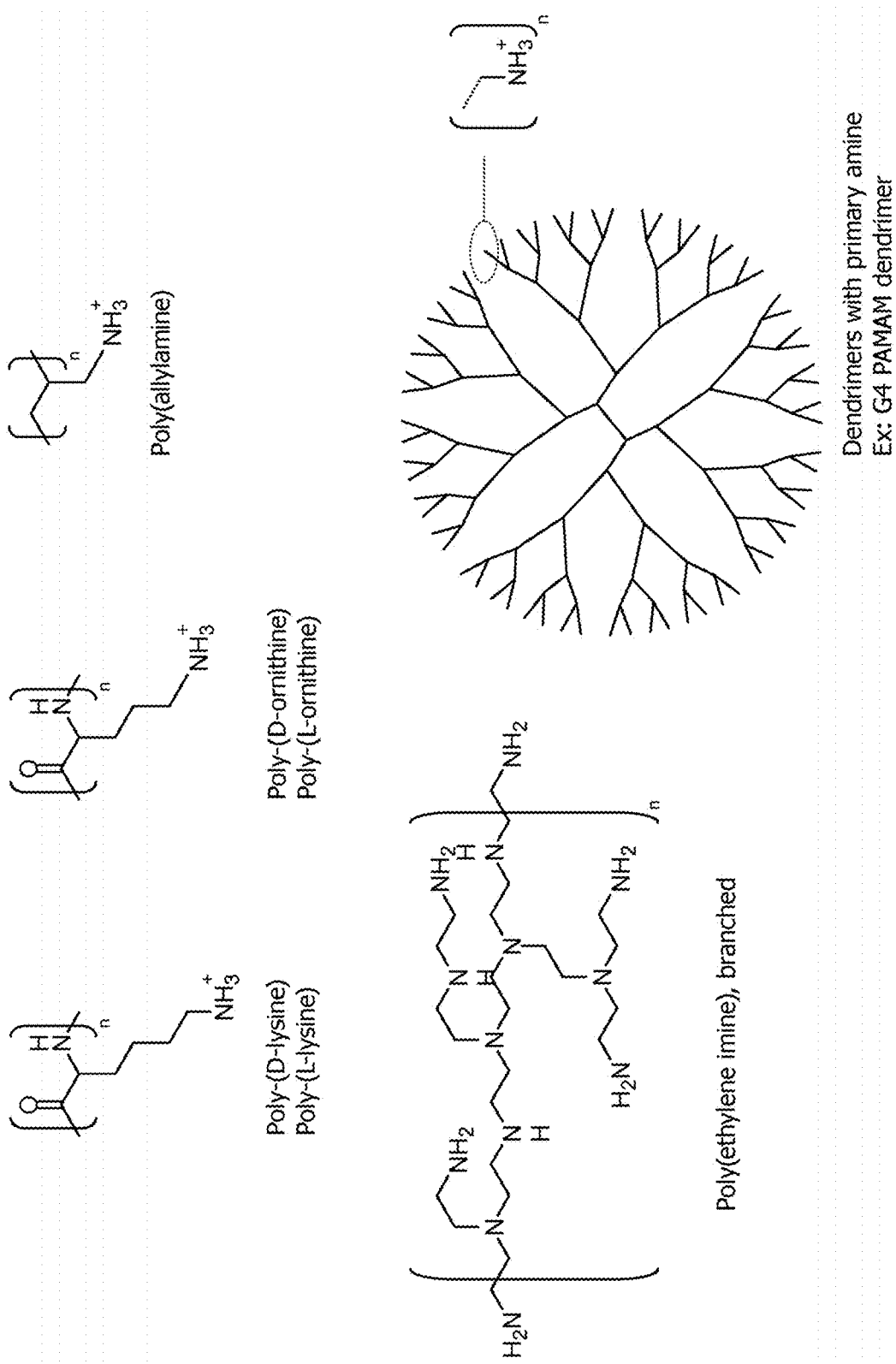
FIG. 2 is a diagram illustrating specific examples of the cationic polymer that can be used in a probe according to the present invention.

The present invention will now be described in detail, but is not limited to the embodiments described in the present specification.

According to a first embodiment, the present invention relates to a probe for distinguishing types and/or amounts of protein and post-translational modification thereto, wherein the probe comprises (1) a cationic polymer comprising at least five primary amino groups in one molecule and having a weight-average molecular weight of 1,000 to 500,000 and (2) an environment-sensitive fluorophore having a naphthalenesulfonic acid structure or a benzofurazan structure, wherein the fluorophore is covalently bonded to some of the primary amino groups in the cationic polymer.

The "protein" which is targeted by the probe of the present embodiment may be any protein consisting of any amino acid sequence, and may be derived from, for example, an animal, plant, microorganism, or virus. Examples of the protein targeted by the probe of the present embodiment include, but not limited to, plasma proteins, such as albumin, fibrinogen, α1-antitrypsin, transferrin, immunoglobulin, and C-reactive protein; enzymes, such as ERK, Akt, MEK, p38, pepsin, amylase, and lipase; and myoglobin, hemoglobin, concanavalin, lactoglobulin, and lactalbumin. In addition, the protein targeted by the probe of the present embodiment may be the entire protein of those mentioned above, or may be a peptide fragment thereof. The amino acid sequence of the peptide fragment may be comprised of any amino acid sequence and may have any length.

The "post-translational modification" which is targeted by the probe of the present embodiment means any modification of a polypeptide translated from mRNA. Examples of the post-translational modification targeted by the probe of the present embodiment include, but are not limited to, phosphorylation, saccharification, acetylation, methylation, acetylation, alkylation, glycosylation, oxidation, citrullination, hydroxylation, ubiquitination, and SUMOylation. The post-translational modification targeted by the probe of the present embodiment may be introduced at any one or more positions of the proteins.

The cationic polymer (1) used in the probe of the present embodiment may be any polymer that has a weight-average molecular weight of 1,000 to 500,000 and comprises at least five primary amino groups in one polymer molecule. Here, the "polymer" means a compound prepared by polymerization of two or more monomers that may be the same or different, and may accordingly be a homopolymer or a copolymer. The polymer may have any degree of polymerization, and the "polymer" therefore includes an oligomer.

The cationic polymer according to the embodiment has a weight-average molecular weight of 1,000 to 500,000, preferably 1,500 to 200,000, and particularly preferably 2,000 to 100,000.

The cationic polymer according to the present embodiment comprises at least five, preferably seven or more, and particularly preferably ten or more primary amino groups in one molecule of the polymer.

The cationic polymer according to the present embodiment is preferably a linear or branched polyamino acid, polyallylamine, polyamidoamine, or polyalkyleneimine. FIG. 2 shows examples of the preferred cationic polymer of the present embodiment. Furthermore, these cationic polymers may be copolymers with polyethylene glycol.

The polyamino acid according to the present embodiment may be a polymer of a single type of amino acid residues or may be a polymer of multiple different types of amino acid residues. In addition, the amino acid residues that constitute the polyamino acid may be in L-form or D-form. Examples of the polyamino acid include polylysine, polyornithine, a random copolymer of lysine and phenylalanine, and a random copolymer of lysine and tyrosine. The polyamino acid according to the present embodiment is preferably polylysine or polyornithine.

Examples of the polyalkyleneimine according to the present embodiment include polyethyleneimine, polypropyleneimine, and polybutyleneimine. The polyalkyleneimine according to the present embodiment is preferably polyethyleneimine.

In the probe of the present embodiment, a fluorophore having a naphthalenesulfonic acid structure or a benzofurazan structure is used as the environment-sensitive fluorophore (2). Here, the "environment-sensitive fluorophore" means a fluorophore that changes the fluorescence properties depending on the surrounding environment of the fluorescent molecule.

Examples of the environment-sensitive fluorophore (2) having a naphthalenesulfonic acid structure used in the probe of the present embodiment include 5-dimethylaminonaphthalene-1-sulfonyl (dansyl), 1-anilinonaphthalene-8-sulfonate (ANS), N-methyl-2-anilinonaphthalene-6-sulfonate (MANS), 2-p-toluidinylnaphthalene-6-sulfonate (TNS), and fluorescent derivatives thereof. The environment-sensitive fluorophore having a naphthalenesulfonic acid structure according to the present embodiment is preferably dansyl or a fluorescent derivative thereof.

Examples of the environment-sensitive fluorophore (2) having a benzofurazan structure used in the probe of the present embodiment include 4-(N,N-dimethylaminosulfonyl)-2,1,3-benzoxadiazole (DBD), 7-nitro-2,1,3-benzoxadiazole (NBD), 4-(aminosulfonyl)-2,1,3-benzoxadiazole (ABD), ammonium 2,1,3-benzoxadiazole-4-sulfonate (SBD), and fluorescent derivatives thereof. The environment-sensitive fluorophore having a benzofurazan structure according to the present embodiment is preferably DBD or a fluorescent derivative thereof.

In the probe of the present embodiment, the environment-sensitive fluorophore (2) is introduced into some of the primary amino groups in the cationic polymer (1) by a covalent bond. Here, "some" means preferably 1% to 50%, particularly preferably 5% to 20% of the primary amino groups in the cationic polymer molecules.

The probe of the present embodiment can be synthesized by a known chemical synthesis method or a chemical synthesis method described in the following Examples or equivalent thereto.

In the probe of the present embodiment, a functional group selected from the group consisting of a guanidium group, a carboxyl group, an alkyl group, an aryl group, and an amino acid may be introduced into at least some of the primary amino groups into which the environment-sensitive fluorophore has not been introduced. The alkyl group according to the present embodiment is preferably $C_{1-10}$ and particularly preferably $C_{1-5}$. The alkyl group may be in a linear or branched chain form. Examples of the aryl group according to the present embodiment include a phenyl group, an indenyl group, a naphthyl group, a diphenylmethyl group, and a triphenylmethyl group. Examples of the amino acid according to the present embodiment include leucine, valine, isoleucine, tyrosine, tryptophane, phenylalanine, serine, asparagine, and glutamine.

According to the present embodiment, the introduction of a functional group into an amino group can be performed by a known chemical synthesis method. The introduction of a guanidium group into an amino group can be performed by, for example, using 1H-pyrazole-1-carboxamidine hydrochloride (Bernatowicz, M. S. et al., J. Org. Chem., 1992, 57 (8), pp. 2497-2502). The introduction of a carboxyl group, an alkyl group, or an aryl group into an amino group can be performed by, for example, acetylation reaction using carboxylic anhydride, such as acetic anhydride, phthalic anhydride, and naphthalene dicarboxylic anhydride. The introduction of an amino acid into an amino group can be performed by, for example, dehydration condensation of the carboxyl group of the amino acid.

The probe of the present embodiment can distinguish types and/or amounts of protein interacted with the cationic polymer (1) and post-translational modification thereto based on the environment sensitivity of the fluorophore (2) having a naphthalenesulfonic acid structure or a benzofurazan structure. Also, the probe of the present embodiment can non-specifically interact with one or more proteins comprised in a sample so as to detect the sum of changes in the protein component of the sample.

According to a second embodiment, the present invention relates to an array for distinguishing types and/or amounts of protein and post-translational modification thereto or for determining the type and/or state and/or concentration of cells being cultured, the array including the above-described probe dissolved in a plurality of solvents having different ionic strengths and/or pH levels and disposed in a plurality of separate sections on a substrate.

The "protein" and the "post-translational modification" targeted by the probe of the present embodiment are the same as those defined in the first embodiment.

In the array of the present embodiment, the probe to be used is dissolved in a plurality of solvents having different ionic strengths and/or pH conditions. The solvents that can be used have, for example, two or more, preferably three or more, particularly preferably six or more different ionic strengths and/or pH conditions. In addition, the array of the present embodiment may be prepared using one type of probe, but is more preferably prepared using a plurality of types of probes, for example, two or more, preferably three or more, and particularly preferably six or more types of probes. Accordingly, for example, four types of probe solutions are prepared by using two types of solvents and two types of probes, and 15 types of probe solutions are prepared by using five types of solvents and three types of probes.

The solvent for dissolving a probe may be an aqueous solvent comprising any buffer and/or salt. Examples of the buffer include MES, MOPS, EPPS, HEPES, Tris, phosphate, acetate, citrate, borate, and glycine buffers. Examples of the salt include NaCl, KCl, $MgCl_2$, $Na_2SO_4$, $K_2SO_4$, $MgSO_4$, NaI, and NaSCN. According to the present embodiment, the pH of the solvent is preferably 4 to 10, and the ionic strength of the solvent is preferably 10 to 500 mM. The concentration of a probe according to the present embodiment is preferably 0.1 to 100 μg/mL.

The array of the present embodiment can be prepared by disposing a probe solution, in which the probe is dissolved in a solvent, on a substrate having a plurality of separate sections. As the substrate, a clear glass or plastic substrate can be used. For example, a multi-well plate, such as a 96-well plastic plate, can be used.

According to a third embodiment, the present invention relates to a method for analyzing a protein-containing sample, comprising (1) dissolving a probe capable of non-specifically interacting with a plurality of proteins in a plurality of solvents having different ionic strengths and/or pH levels, wherein the probe comprises (a) a cationic polymer comprising at least five primary amino groups in one molecule and having a weight-average molecular weight of 1,000 to 500,000 and (b) an environment-sensitive fluorophore having a naphthalenesulfonic acid structure or a benzofurazan structure, wherein the fluorophore is covalently bonded to some of the primary amino groups in the cationic polymer; (2) adding a test sample comprising one or more proteins to a plurality of probe solutions prepared in the step (1), thereby the proteins in the test sample and the probe are interacted non-specifically; (3) measuring the fluorescence intensities of the plurality of probe solutions to which the test sample has been added in the step (2); and (4) comparing the pattern of fluorescence intensities obtained in the step (3) with the pattern of fluorescence intensities obtained from a reference sample.

The "protein", "probe", "polymer", "cationic polymer", and "environment-sensitive fluorophore" according to the present embodiment are the same as those defined in the first embodiment.

In the method of the present embodiment, the above-described probe is dissolved in a plurality of solvents having different ionic strengths and/or pH levels. Here, the probe of the present embodiment can non-specifically interact with a plurality of proteins, and the term "a plurality of proteins" can include not only one or more different types of proteins, but also identical proteins different in the type and/or amount of a post-translational modification. In addition, the "solvent" according to the present embodiment is the same as that defined in the second embodiment, and a probe solution can be prepared as described above. In addition, as described above, a plurality of solvents and a plurality of types of probes can be used, and higher multidimensional data can be obtained by increasing the numbers of solvent types and probe types. For example, six-dimensional data can be obtained by using three types of probes and two types of solvents, and 15-dimensional data can be obtained by using five types of probes and three types of solvents.

Subsequently, a test sample comprising one or more proteins is added to a plurality of probe solutions. The final protein concentration to be added may be 1 nM to 1 mM and preferably 5 nM to 10 μM. When the protein concentration in the test sample is unknown, the sample may be appropriately serially diluted and then added. Here, the test sample may contain a single type of protein or may contain a plurality of types of proteins, and the proteins may contain any one or more post-translational modifications. Examples of the protein-containing sample include biological fluid samples, such as blood, serum, plasma, urine, saliva, cell lysate, and cell secretion solution; and a cell culture supernatant. In this step, the probe non-specifically interacts with proteins contained in a sample, regardless of the type of the protein and the type of post-translational modification.

Subsequently, the fluorescence intensities of the plurality of probe solutions after adding the test sample are measured. In the method of the present embodiment, the fluorescence intensities can be measured at an excitation wavelength of 300 to 500 nm and an emission wavelength of 400 to 700 nm. In addition, in the method of the present embodiment, for each measuring object, fluorescence intensities at a plurality of sets of excitation wavelength/emission wavelength (e.g., excitation wavelength (nm)/emission wavelength (nm): 320/520, 340/480, 340/520, and 340/540) are preferably measured. For example, fluorescence intensities at two sets, three sets, or four sets of excitation wavelength/emission wavelength can be measured.

The fluorescence intensity measured in the above varies depending on the type of protein contained in the sample and post-translational modification thereto, and also varies depending on the conditions of the solvent in which the probe is dissolved. Accordingly, a unique pattern of fluorescence intensities (fluorescent fingerprint) for the sample can be obtained by this step.

Subsequently, the pattern of fluorescence intensities obtained from the test sample is compared with the pattern of fluorescence intensities obtained from a reference sample. The pattern of fluorescence intensities of a reference sample may be obtained by measuring fluorescence intensities concurrently with those of a test sample, or a predetermined pattern of fluorescence intensities in advance may be used. The comparison of pattern of fluorescence intensities can be preferably performed by compressing the dimension number by multivariate analysis, such as principal component analysis, linear discriminant analysis, or hierarchical clustering analysis, and compressing and converting the difference between the fluorescent fingerprints into two-dimensions or three-dimensions.

The method of the present embodiment can analyze a sample based on only the difference in pattern of fluorescence intensities. Accordingly, the composition of proteins in the reference sample of the present embodiment may be identified or may not be identified. If the composition of proteins in the reference sample is identified, types and/or amounts of protein and post-translational modification thereto in a test sample can be determined based on the difference in the pattern of fluorescence intensities. Even if the composition of proteins in the reference sample is not identified, it is possible to analyze a sample containing proteins based on the difference in pattern of fluorescence intensities.

Thus, according to a specific embodiment, types and/or amounts of protein and post-translational modification thereto in a test sample can be determined. In this case, it is preferable to use a reference sample of which types and/or amounts of protein and post-translational modification thereto are specified.

The outline of the specific embodiment is shown in FIG. 1. FIG. 1 shows a probe (PLL-Dnc) prepared by introducing dansyl into poly-L-lysine, and a probe (PLL-DBD) prepared by introducing dimethylaminosulfonyl benzoxadiazole into poly-L-lysine, as the examples of the probes. The fluorescence intensities of these probes are increased by interactions with a protein (e.g., BSA (without post-translational modification), BSA-Phos (phosphorylated), or BSA-Me (methylated)), and the degree of increase varies according to the type/amount of the post-translational modification (FIG. 1, middle panel). Furthermore, since the amount of change in the fluorescence intensity of the probe also varies depending on the conditions of the solvent dissolving the probe, the pattern of fluorescence intensities (fluorescent fingerprint) unique to a protein of interest can be obtained by using a plurality of different solvents (FIG. 1, lower panel). Accordingly, types and/or amounts of protein and post-translational modification thereto in a test sample can be determined by using a reference sample of which types and/or amounts of protein and post-translational modification thereto are predetermined. For example, when BSA, BSA-Phos, and BSA-Me are used as reference samples, if the fluorescent fingerprint obtained from a test sample is stochastically most approximate to the fluorescent fingerprint distribution obtained from the BSA-Phos, it is estimated or specified that the BSA in the test sample is phosphorylated. Also, for example, the phosphorylation ratio of BSA in a test sample can be quantified by using mixtures of BSA and BSA-Phos at different ratios as reference samples and by using a standard curve generated based on the results of linear discriminant analysis of the resulting fluorescent fingerprints of the reference samples.

In addition, according to a specific embodiment, the type and/or state and/or concentration of cells being cultured can be determined by using a cell culture supernatant as the test sample. When cells are cultured in a medium containing serum, the cells generate a variety of proteins and secret them in the medium, while consuming serum protein in the medium. Since the consumption and secretion (COnsumption and RElease: CORE) profile of the cells is variable with the type or the state of the cells, the type/state/concentration of the cells can be specified based on the CORE profile obtained by analysis of the cell culture supernatant. Here, in conventional metabolomic analysis methods, a variety of proteins present in a cell culture supernatant are respectively quantitatively analyzed to obtain the CORE profile of the cells. In contrast, in the method of the present embodiment, a pattern of fluorescence intensities (fluorescent fingerprint) reflecting the sum of non-specific interactions between a probe and various proteins present in a cell culture supernatant is obtained and is compared with the pattern of fluorescence intensities of a reference sample to detect a change in the CORE profile.

That is, in a specific embodiment, the reference sample is preferably, for example, a fresh medium before culturing cells, or a cell culture supernatant obtained from a culture in which the type and/or state and/or concentration of the cells are known.

Figure 21:
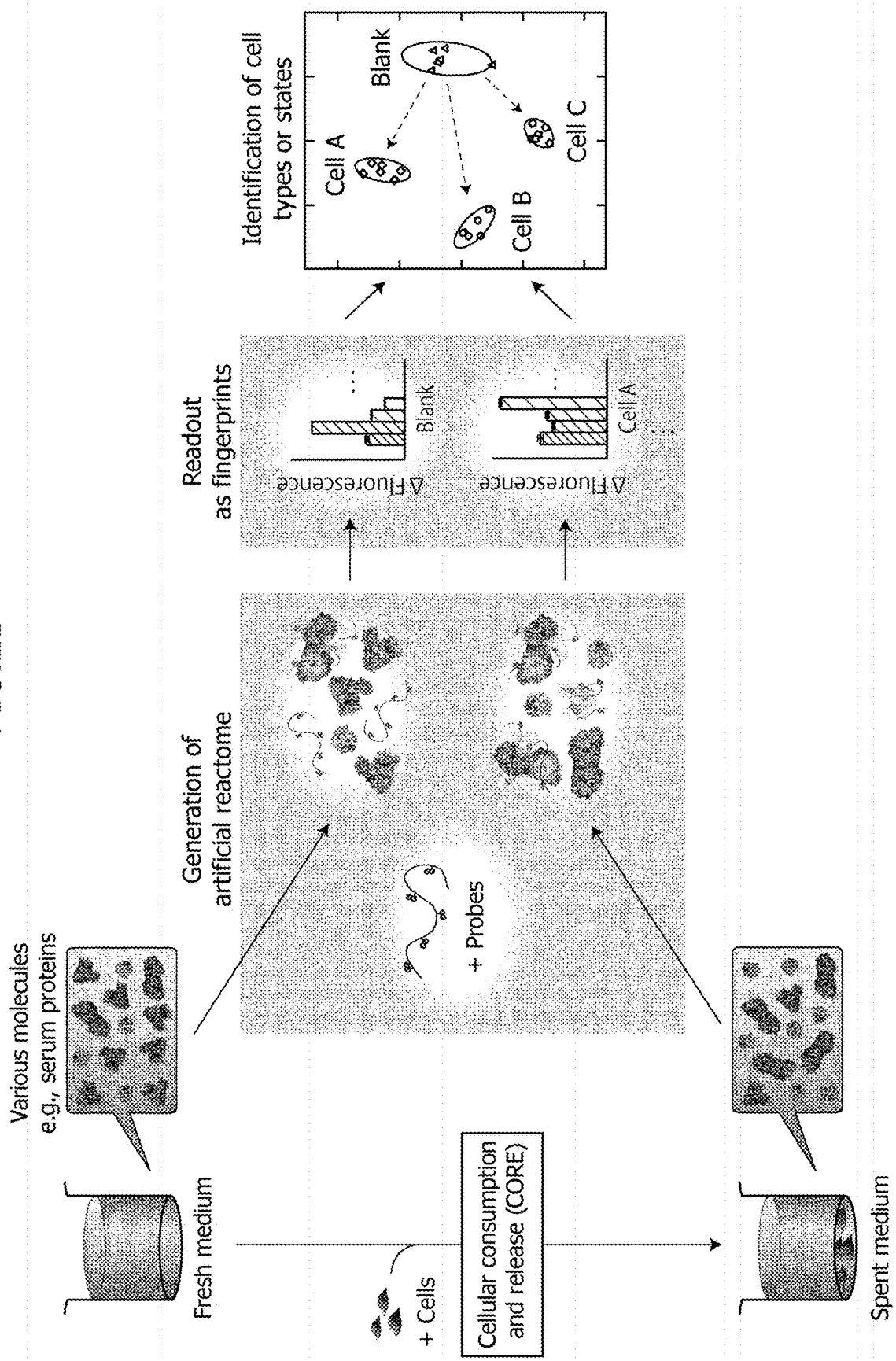
FIG. 21 is a schematic diagram illustrating the principle of a method for determining the type and/or state and/or concentration of cells being cultured by an embodiment of the present invention.

The outline of the above-described specific embodiment is shown in FIG. 21. FIG. 21 shows an example of using a cell culture supernatant as the test sample. The probe according to the present embodiment non-specifically interacts with various proteins contained in a cell culture supernatant, and the sum of the interactions is measured as the fluorescence intensity. This fluorescence intensity changes according to the composition of proteins contained in the culture medium. Accordingly, the type and/or state and/or concentration of cells being cultured can be determined by comparing the pattern of fluorescence intensities obtained from the cell culture supernatant. For example, a fresh medium and culture supernatants of cells A, B, and C are used as reference samples. If the fluorescent fingerprint obtained from a test sample is stochastically most approximate to the fluorescent fingerprint distribution obtained from the cell A, the test sample is estimated or specified as a culture supernatant of the cell A. In addition, for example, mixtures of cell A and cell B at different ratios are used as reference samples, and a standard curve is generated based on the results of linear discriminant analysis of the resulting fluorescent fingerprints of the reference samples. The mixture ratio of cell A and cell B in the culture of a test sample can be identified by using the standard curve.

Furthermore, according to a specific embodiment, the state of cells being cultured is preferably a degree of cell differentiation. Currently, the degree of cell differentiation is generally determined by quantifying the expression of a specific differentiation marker protein. In contrast, the method of the present embodiment uses a probe non-specifically interacting with a plurality of proteins and detects the sum of changes in the protein component in a cell culture supernatant with the cell differentiation as a change in the pattern of fluorescence intensities.

That is, in a specific embodiment, the reference sample is preferably, for example, a supernatant collected from a culture of undifferentiated cells, a supernatant collected from a culture of cells of which differentiation state is known, or a supernatant collected a culture of cells after a certain period of time has elapsed since differentiation induction. For example, supernatants of undifferentiated cells and differentiated cells are used as reference samples, and if the fluorescent fingerprint obtained from a test sample is stochastically most approximate to the fluorescent fingerprint distribution obtained from the differentiated cells, the test sample is estimated or specified as a culture supernatant of the differentiated cells.

According to the specific embodiment described above, the degrees of differentiation of various cell species can be determined using only one or a few types of probes without necessity of specifying and/or quantifying the differentiation marker protein. In addition, since a culture supernatant is used as the test sample, the degree of cell differentiation can be determined noninvasively. Thus, it is also possible to track the degrees of differentiation over time for a specific culture.

The array in the second embodiment and the method in the third embodiment can distinguish and quantify one or more post-translational modifications in a single protein or a plurality of proteins contained in a sample easily and with high efficiency using only one or a few probes. In addition, when a cell culture supernatant is used as a test sample, the type and/or state and/or concentration of cells being cultured can be distinguished with high accuracy and noninvasively.

EXAMPLES

The present invention will now be further described with Examples, but is not limited to the following Examples.

1. Synthesis of Probe

Figure 3A:
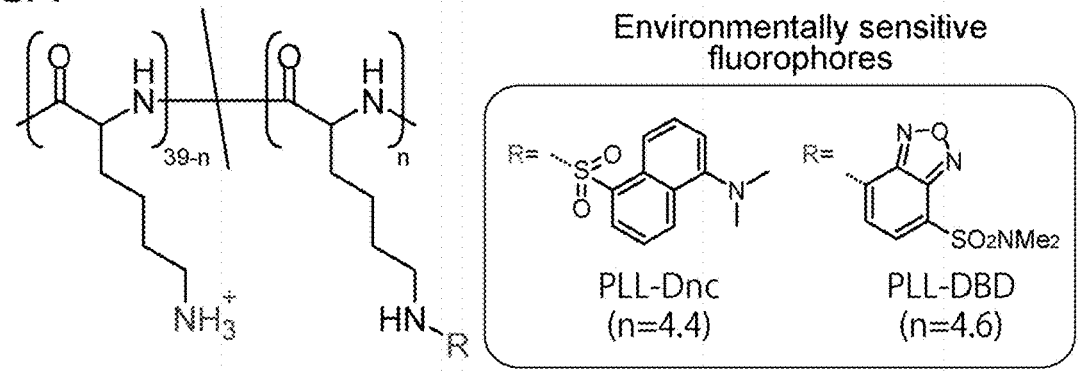
FIG. 3 is a diagram illustrating structural formulae of probes (Compounds 1 to 7) synthesized in Examples.
Figure 3B:
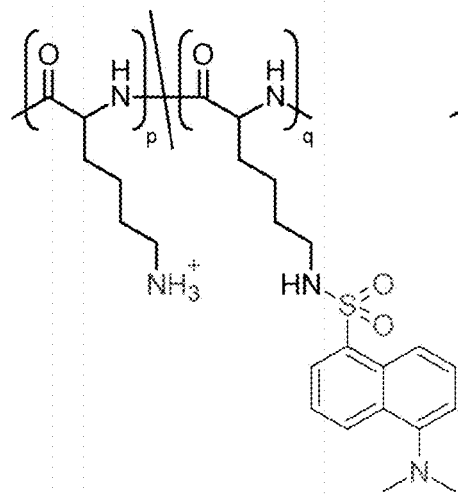
Figure 3C:
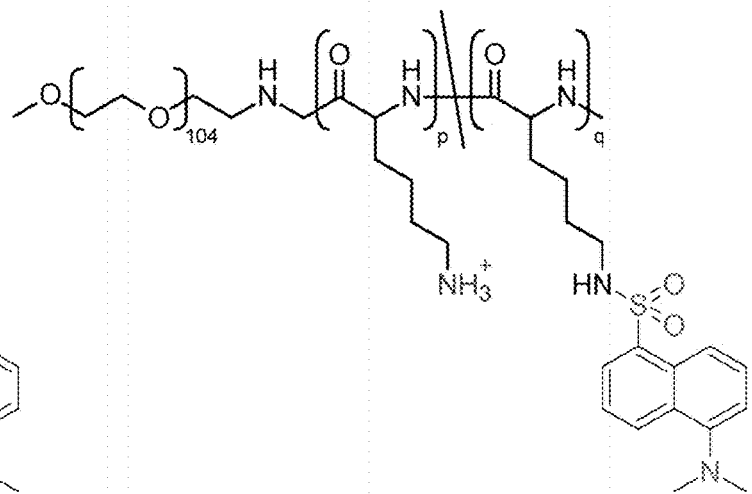
Figure 3D:
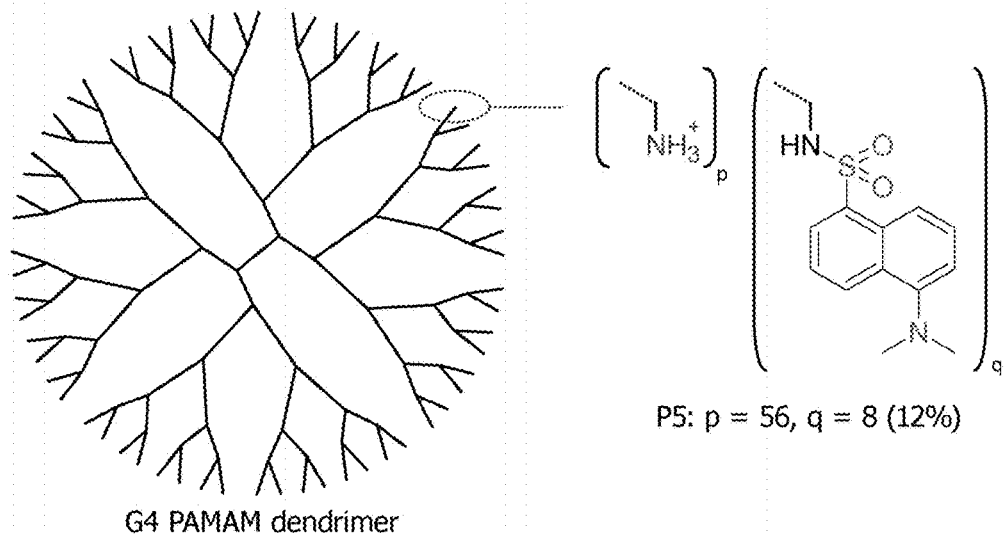
Figure 4A:
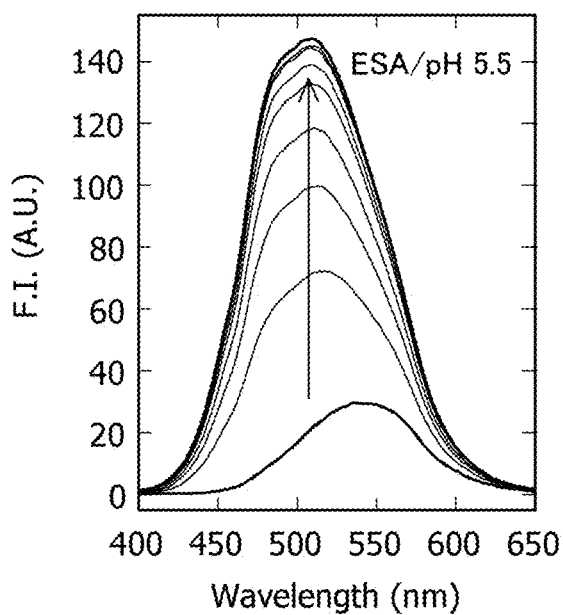
FIG. 4 shows graphs showing the results of characterization for PLL-Dnc (Compound 1).
Figure 4B:
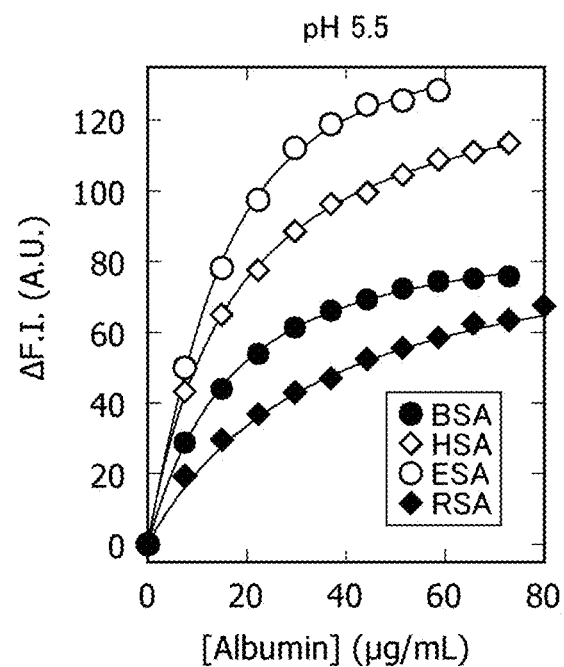
Figure 4C:
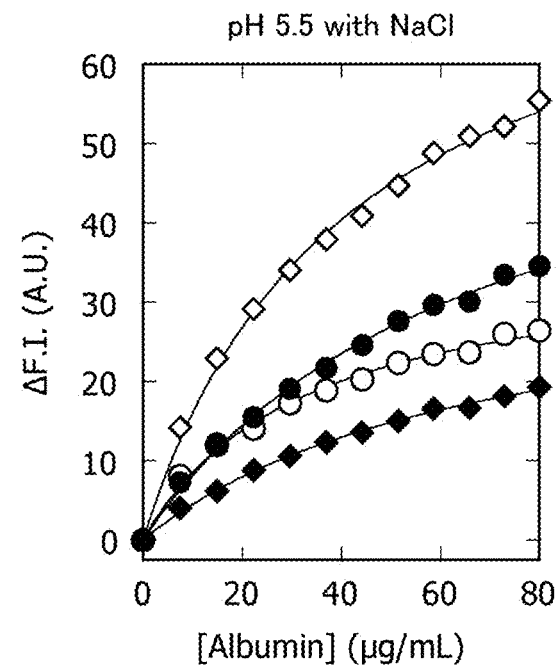
Figure 4D:
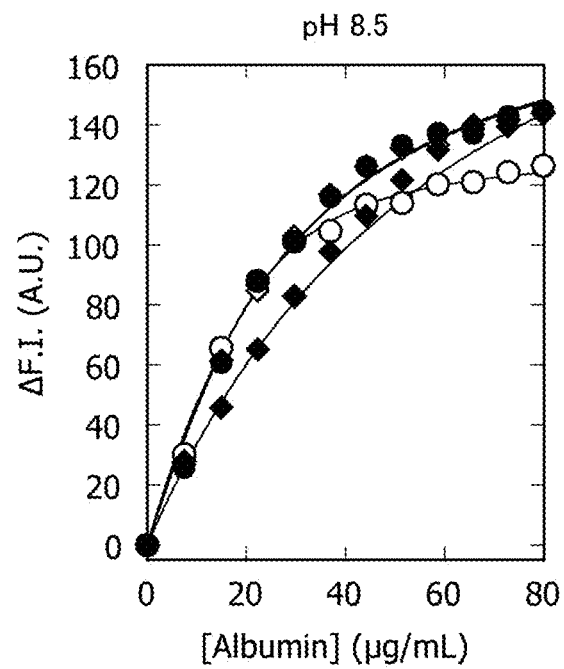

Probes prepared by introducing dansyl (Dnc) into poly-L-lysine (PLL) (Compound 1 (FIG. 3(a)) and Compounds 3 to 5: P1 to P3 (FIG. 3(b))); a probe prepared by introducing dimethylaminosulfonyl benzoxadiazole (DBD) into PLL (Compound 2, FIG. 3(a)); a probe prepared by introducing Dnc into a block copolymer of polyethylene glycol and PLL (Compound 6: P4, FIG. 3(c)); and a probe prepared by introducing Dnc into a PAMAM dendrimer (Compound 7: P5, FIG. 3(d)) were obtained by the procedures disclosed below.

(1-1) Synthesis of PLL-Dnc (Compound 1)

20 mg of poly-L-lysine hydrobromate (Mw: 8.2 k, number of units: 39) (Sigma-Aldrich) was dissolved in 5 mL of methanol, triethylamine in an amount of five times the amount of the amino groups of the poly-L-lysine was added to the solution with stirring, and 0.67 mL of 20 mM 5-(dimethylamino)naphthalene-1-sulfonyl chloride (Dnc-Cl) (Tokyo Chemical Industry Co., Ltd.) in THF solution was further added thereto. Subsequently, the mixture was sealed and shielded from light and stirred at room temperature for 24 hours. The reaction solution was placed in a dialysis tube (Spectra/Por6, MWCO: 8 kDa, Spectrum) and was dialyzed in sequence against 10% methanol, distilled water, 1 mM HCl, and distilled water. Subsequently, lyophilization was performed to obtain a powder of a probe (PLL-Dnc (Compound 1)), in which Dnc was introduced into PLL.

(1-2) Synthesis of PLL-DBD (Compound 2)

A powder of a probe (PLL-DBD (Compound 2)) in which DBD was introduced into PLL was prepared by the same procedure as in the above (1) except that 4-(N,N-dimethylaminosulfonyl)-7-fluorobenzoxadiazole (DBD-F) (Tokyo Chemical Industry Co., Ltd.) was used instead of Dnc-Cl.

(1-3) Synthesis of Probes (Compounds 3 to 7: P1 to P5) in which Dnc was Introduced into Various Cationic Polymers As cationic polymers, PLLs having different molecular weights (number of units: 10, 55, and 258) (Alamanda Polymers, Inc.), a block copolymer of polyethylene glycol and PLL (number of polyethylene glycol units: 104, number of PLL units: 52) (Alamanda Polymers, Inc.), and a PAMAM dendrimer (ethylene diamine core, the 4.0 generation) (Sigma-Aldrich) were used. To a 4 mg/mL cationic polymer in MeOH solution was added triethylamine in an amount of five times the amount of the amino groups of the cationic polymer with stirring, and thereto was further added dansyl chloride (THF solution) in an amount of 0.15 times the amount of the amino groups of the cationic polymer. Probes (Compounds 3 to 7: P1 to P5) introduced with Dnc were prepared by the same procedure as in the above (1), excluding the above.

2. Characterization of Probes

Proteins were interacted with Compounds 1 to 7 to evaluate the fluorescence properties. The proteins used were albumins derived from various animals (bovine serum albumin (BSA), human serum albumin (HSA), and rabbit serum albumin (RSA) (all purchased from Sigma-Aldrich), and equine serum albumin (ESA) (Rockland Immunochemicals, Inc.) and human plasma-derived α1-antitrypsin (Ant) (Sigma-Aldrich)).

(2-1) Characterization of PLL-Dnc (Compound 1)

Compound 1 was dissolved in 18 mM MES (pH 5.5) to give a concentration of 5 µg/mL. 2 mL of the resulting probe solution was placed in a quartz cell with a 1 cm optical path, and 2.5 mg/mL ESA aqueous solution was dropwise added thereto. At every dropping of the ESA aqueous solution, the solution was sufficiently stirred and left to stand at room temperature for 3 minutes, and the fluorescence spectrum was measured at an excitation wavelength of 340 nm and an emission wavelength of 400 to 650 nm.

The results are shown in FIG. 4 (a). It was demonstrated that PLL-Dnc (Compound 1) showed only weak fluorescence in the absence of ESA; however, the addition of ESA led to emission of fluorescence, and the fluorescence intensity significantly increased with increasing the concentration of ESA.

Next, Compound 1 was dissolved in the following three solvents: (1) 18 mM MES (pH 5.5), (2) 18 mM EPPS (pH 8.5), or (3) 18 mM MES+25 mM NaCl (pH 5.5), to prepare probe solutions (5 µg/mL). An aqueous solution (2.5 mg/mL) of BSA, HSA, RSA, or ESA was dropwise added to each probe solution, and the fluorescence intensities were measured by the same procedure as in the above at an excitation wavelength of 340 nm and an emission wavelength of 510 nm.

The results are shown in FIG. 4 (b) to (d). FIG. 4 (b), FIG. 4 (c), and FIG. 4 (d) show the results of measurement with the probe solution of the above (1), the probe solution of the above (2), and the probe solution of the above (3), respectively. The vertical axis (ΔF.I.) represents the amount of change in the fluorescence intensity by addition of each protein. PLL-Dnc (Compound 1) interacted with all of BSA, HSA, RSA, and ESA and emitted fluorescence. In addition, the amount of increase in the fluorescence intensity largely changed according to the solvent conditions. In FIG. 4 (d), the amounts of increase in the fluorescence intensity by BSA and HSA were almost the same, and the curves of the graphs of the both overlap with each other. This result suggests that PLL-Dnc (Compound 1) can be used as a turn-on type fluorescent probe that can detect and discriminate a protein with a high S/N ratio.

(2-2) Characterization of PLL-DBD (Compound 2)

Compound 2 was dissolved in 18 mM MES (pH 5.5) to give a concentration of 5 g/mL to prepare a probe solution. ESA was added to the solution by the same procedure as in the above (2-1), and the fluorescence spectrum (500 to 700 nm) and the fluorescence intensity (560 nm) were measured at an excitation wavelength of 440 nm.

Figure 5A:
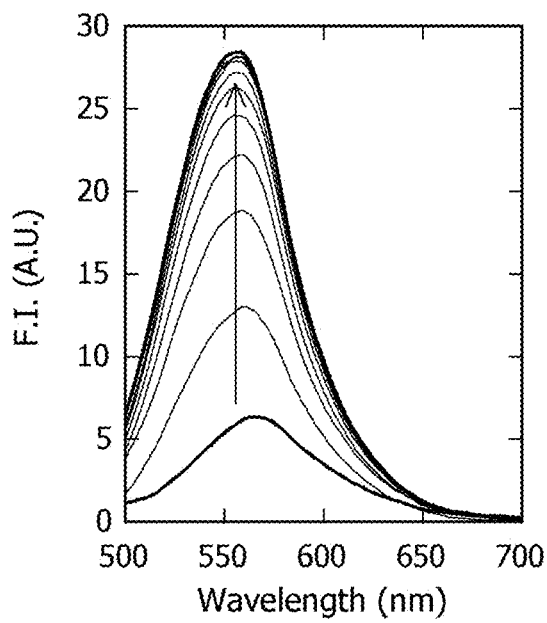
FIG. 5 shows graphs showing the results of characterization for PLL-DBD (Compound 2).
Figure 5B:
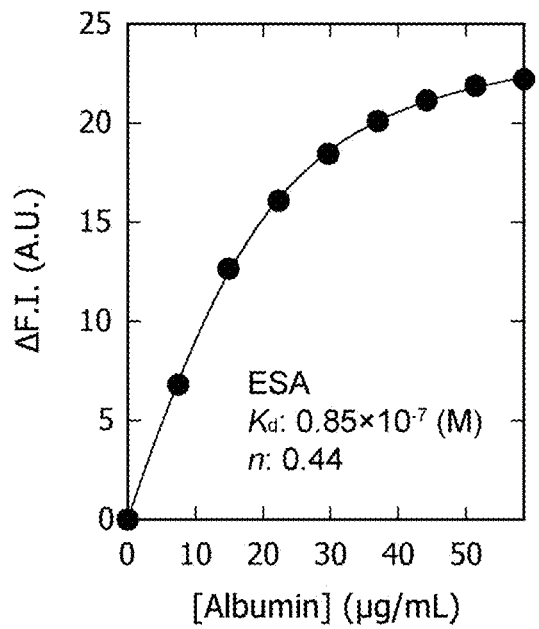

The results are shown in FIG. 5. The vertical axis (ΔF.I.) of FIG. 5 (b) represents the amount of change in the fluorescence intensity by addition of a protein. It was demonstrated that PLL-DBD (Compound 2) also showed only weak fluorescence in the absence of a protein, but the addition of ESA led to emission of fluorescence (FIG. 5 (a)), and the fluorescence intensity significantly increased with increasing the concentration of ESA (FIG. 5 (b)). This result suggests that PLL-DBD (Compound 2) also can be used as a turn-on type fluorescent probe that can detect a protein with a high S/N ratio, as in PLL-Dnc (Compound 1).

(2-3) Characterization of Probes (Compounds 3 to 7: P1 to P5) in which Dnc was Introduced into Various Cationic Polymers Compounds 3 to 7 (P1 to P5) were dissolved in 18 mM MES (pH 5.5) or 18 mM EPPS (pH 8.5) to give a concentration of 1 µg/mL to prepare probe solutions. HSA or Ant was added to each probe solution by the same procedure as in the above (2-1), and the fluorescence spectrum (480 to 675 nm) and the fluorescence intensity (510 nm) were measured at an excitation wavelength of 340 nm.

Figure 6:
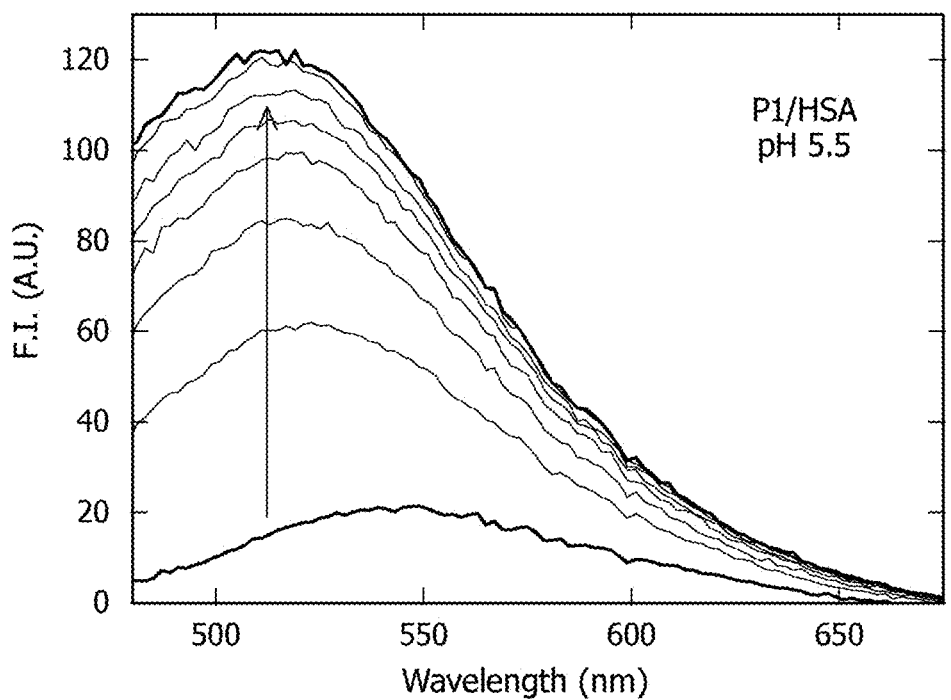
FIG. 6 shows a graph showing the results of characterization for PLL (number of units: 10)-Dnc (Compound 3: P1).
Figure 7A:
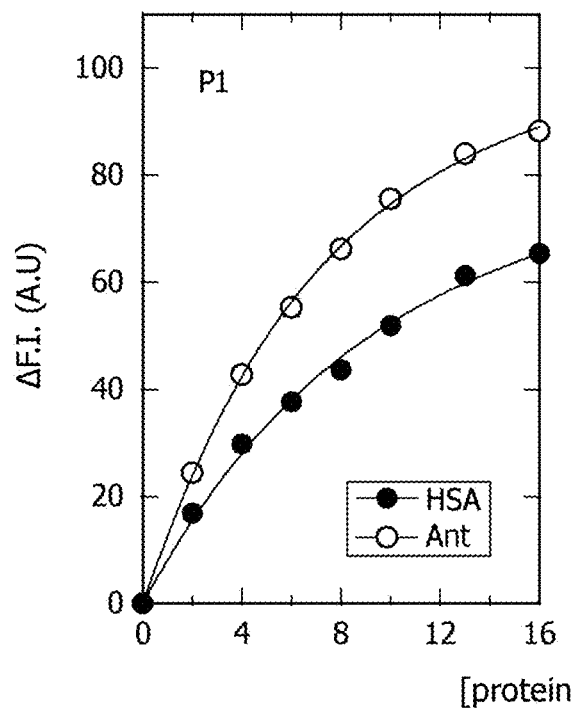
FIG. 7 shows graphs showing the results of characterization for PLL (number of units: 10)-Dnc (Compound 3: P1) and PLL (number of units: 55)-Dnc (Compound 4: P2).
Figure 7B:
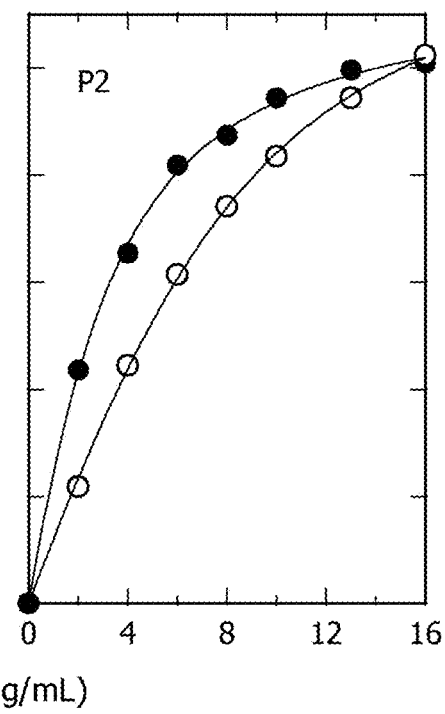

The results of Compound 3 (P1)/pH 5.5 are shown in FIGS. 6 and 7 (a), the results of Compound 4 (P2)/pH 5.5 are shown in FIG. 7 (b), the results of Compound 5 (P3)/pH 5.5 are shown in FIG. 8 (a), the results of Compound 6 (P4)/pH 5.5 are shown in FIG. 8(b), the results of Compound 7 (P5)/pH 5.5 are shown in FIG. 8 (c), the results of Compound 5 (P3)/pH 8.5 are shown in FIG. 8 (d), and the results of Compound 6 (P4)/pH 8.5 are shown in FIG. 8 (e).

The vertical axis (ΔF.I.) of FIG. 7 and the vertical axis (I-I₀) of FIG. 8 represent the amount of change in the fluorescence intensity by addition of a protein. It was also suggested that Compounds 3 to 7 (P1 to P5) also can be used as turn-on type fluorescent probes that can detect a protein with a high S/N ratio as in PLL-Dnc (Compound 1) and PLL-DBD (Compound 2).

3. Discrimination of Different Proteins

Subsequently, it was tested whether different proteins can be discriminated from each other using the probes of Compounds 1 to 7.

(3-1) Discrimination of Albumin by PLL-Dnc (Compound 1).

Probe solutions (5 μg/mL) were prepared by dissolving Compound 1 in the following six types of solvents: (1) 18 mM MES (pH 5.5), (2) 18 mM MOPS (pH 7.0), (3) 18 mM EPPS (pH 8.5), (4) 18 mM MES+25 mM NaCl (pH 5.5), (5) 18 mM MOPS+25 mM NaCl (pH 7.0), and (6) 18 mM EPPS+25 mM NaCl (pH 8.5). An aqueous solution of 20 μg/mL of BSA, HSA, RSA, ESA, or ovalbumin (OVA) (Sigma-Aldrich) or bovine-derived lactalbumin (BLA) (Sigma-Aldrich) was added to each probe solution by the same procedure as in the above (2-1), followed by mixing. After incubation at 30° C. for 10 minutes, fluorescence intensities were measured at the following four sets of excitation wavelength (nm)/emission wavelength (nm): (Ch1) 320/520, (Ch2) 340/480, (Ch3) 340/520, and (Ch4) 340/540. The measurement was repeated six times for each protein.

TABLE 1

Characteristics of albumin

| Origin | Abbreviation | Isoelectric point | Mw (×10³) | Degree of surface hydrophobicity |
|---|---|---|---|---|
| Bovine serum | BSA | 5.6 | 68 | 0.255 |
| Human serum | HSA | 5.7 | 57 | 0.275 |
| Rabbit serum | RSA | 5.7 | 66 | 0.247 |
| Equine serum | ESA | 5.7 | 66 | 0.250 |
| Albumen | OVA | 5.2 | 43 | 0.253 |
| Milk | BLA | 4.8 | 14 | 0.294 |

Figure 9:
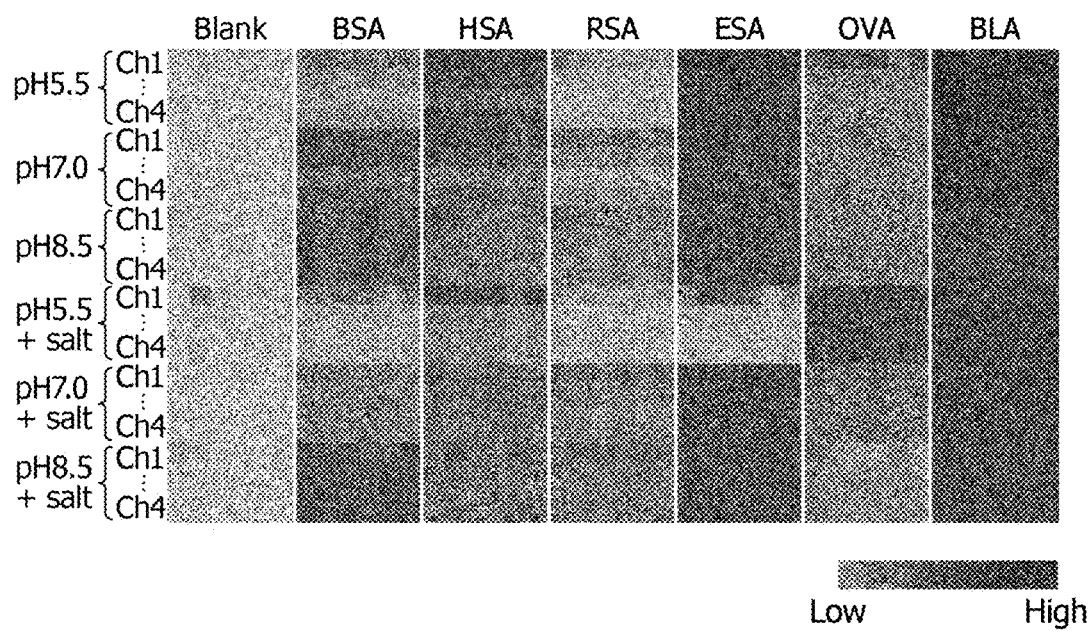
FIG. 9 is a diagram showing fluorescent fingerprints obtained by adding various albumins each to probe solutions prepared by dissolving PLL-Dnc (Compound 1) in six types of solvents and measuring fluorescence intensities at four sets of different excitation wavelengths and emission wavelengths.

The results are shown in FIG. 9. The fluorescence properties of PLL-Dnc (Compound 1) change differently depending on the type of albumin with which interacts and the solvent conditions, and a unique fluorescent fingerprint was obtained from each of different albumins.

Figure 10:
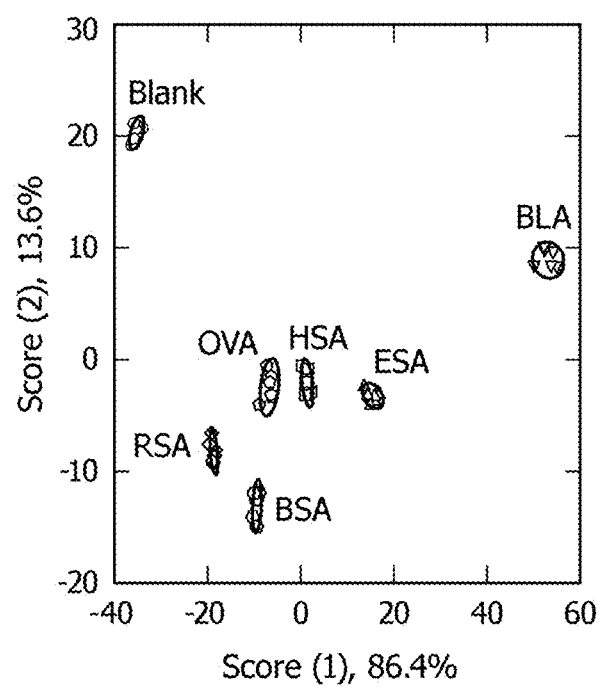
FIG. 10 is a graph obtained by analyzing the results shown in FIG. 9 (solvent conditions: pH 5.5, pH 7.0, and pH 8.5) by linear discriminant analysis and plotting the resulting quadratic discriminant scores.

FIG. 10 shows the results obtained by analyzing the fluorescent fingerprints obtained from the fluorescence intensities (Ch1) in the probe solutions (1) to (3) by linear discriminant analysis, and plotting the resulting quadratic discriminant scores. The respective clusters of the albumins were distributed without overlapping. The results were further analyzed by a jackknife method to verify that each albumin can be discriminated with an accuracy of 100%. The above results verified that one type of probe of PLL-Dnc (Compound 1) can discriminate albumin homologues by only changing the solvent conditions.

(3-2) Discrimination of Albumin by PLL-DBD (Compound 2)

Fluorescent fingerprints were obtained and analyzed by linear discriminant analysis as in the above (3-1) except that Compound 2 was used instead of Compound 1.

Figure 11:
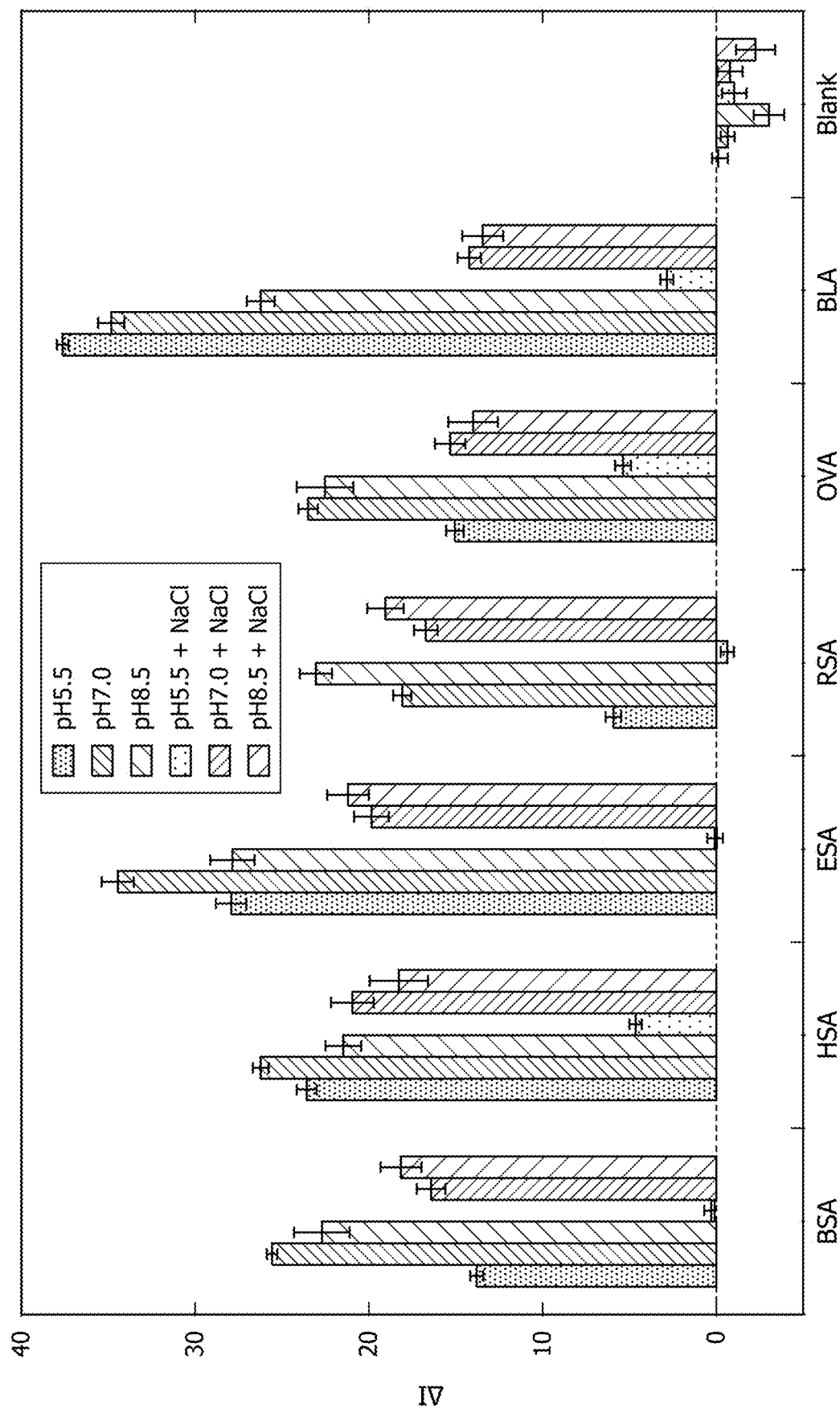
FIG. 11 is a graph showing the amounts of change in fluorescence intensity when various albumins were each added to probe solutions prepared by dissolving PLL-DBD (Compound 2) in six types of solvents.

The results of measurement are shown in FIG. 11. The vertical axis (ΔI) in FIG. 11 represents the amount of increase in the fluorescence intensity (Ch1) by addition of a protein, and six columns for each albumin correspond to probe solutions (1) to (6) from the left, respectively. The results demonstrated that a unique fluorescent fingerprint is obtained from each of different albumins even if PLL-DBD (Compound 2) is used.

Figure 12:
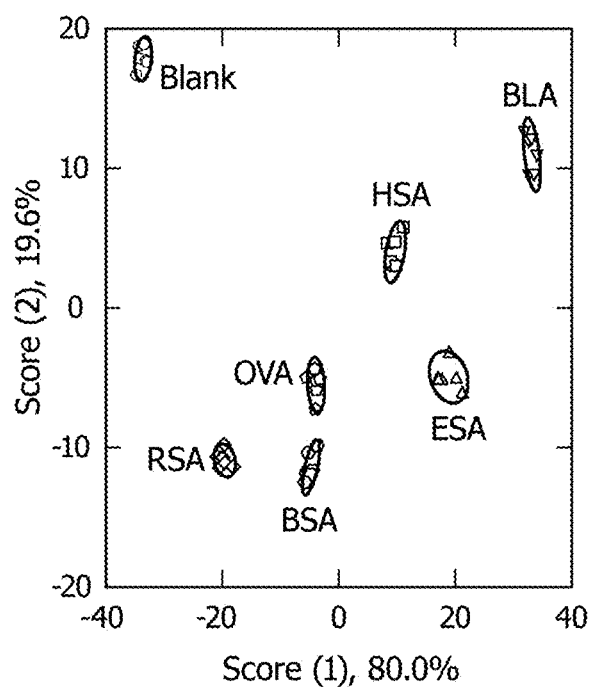
FIG. 12 is a graph obtained by analyzing the results shown in FIG. 11 (solvent conditions: pH 5.5, pH 7.0, and pH 8.5) by linear discriminant analysis and plotting the resulting quadratic discriminant scores.

FIG. 12 shows the results obtained by analyzing the fluorescent fingerprints obtained from the fluorescence intensities (Ch1) in probe solutions (1) to (3) by linear discriminant analysis, and plotting the resulting quadratic discriminant scores. The respective clusters of the albumins were distributed without overlapping. The results were further analyzed by a jackknife method to verify that each albumin can be discriminated with an accuracy of 100%. The above results verified that one type of probe of PLL-DBD (Compound 2) also can discriminate albumin homologues by only changing the solvent conditions, as in PLL-Dnc (Compound 1).

(3-3) Discrimination of Different Proteins by Probes (Compounds 3 to 7: P1 to P5) in which Dnc was Introduced into Various Cationic Polymers Five probes of Compounds 3 to 7 (P1 to P5) were dissolved in (1) 18 mM MES (pH 5.5) or (2) 18 mM EPPS (pH 8.5) to prepare probe solutions. The proteins used as the analysis objects were the following eight plasma proteins: BSA, ESA, RSA, HSA, Ant, human fibrinogen (Fib) (Sigma-Aldrich), human immunoglobulin G (IgG) (Sigma-Aldrich), and human transferrin (Tra) (Sigma-Aldrich). The fluorescence intensities were measured at an excitation wavelength of 340 nm and an emission wavelength of 520 nm (repeated six times for each protein). The resulting fluorescent fingerprints were analyzed by linear discriminant analysis.

Figure 13:
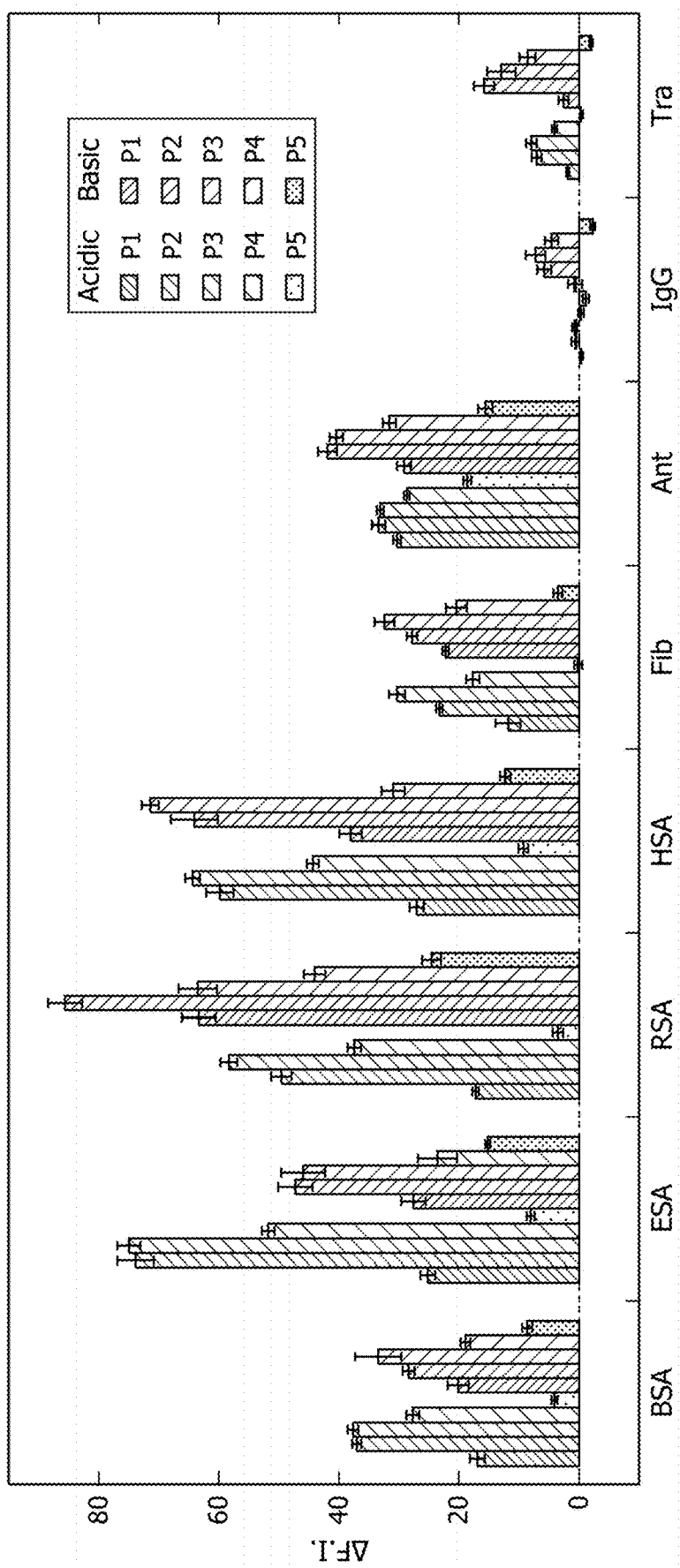
FIG. 13 is a graph showing the amounts of change in fluorescence intensity when five human plasma proteins and three mammalian serum albumins were each added to probe solutions prepared by dissolving probes (Compounds 3 to 7: P1 to P5) in two types of solvents.
Figure 14:
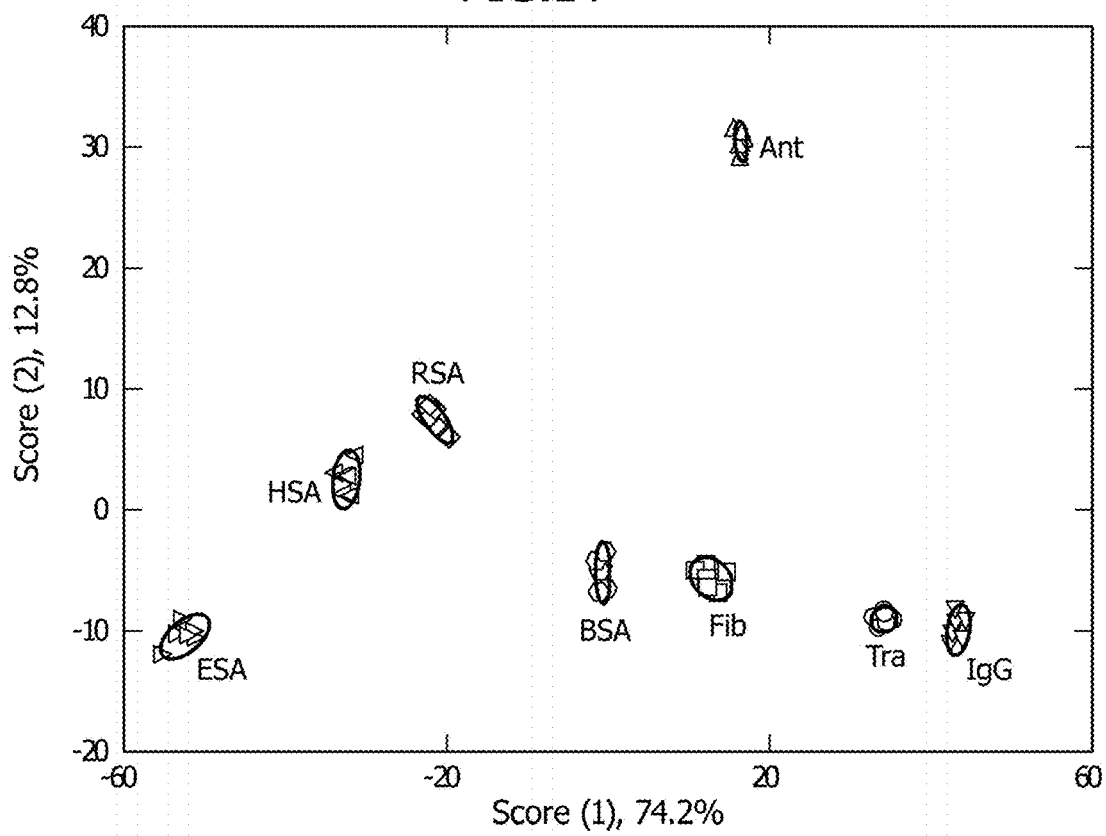
FIG. 14 is a graph obtained by analyzing the results shown in FIG. 13 by linear discriminant analysis and plotting the resulting quadratic discriminant scores.

The results of measurement (two solvent conditions×five probes) are shown in FIG. 13. The vertical axis (ΔF.I.) represents the amount of change in the fluorescence intensity by addition of a protein. In addition, FIG. 14 shows the results of analysis of the measurement results by linear discriminant analysis. The respective clusters of the proteins were distributed without overlapping. The results were further analyzed by a jackknife method to verify that each protein can be discriminated with an accuracy of 100%. In addition, each protein was able to be discriminated with an accuracy of 100% also by a blind test based on the Mahalanobis distance.

Figure 15:
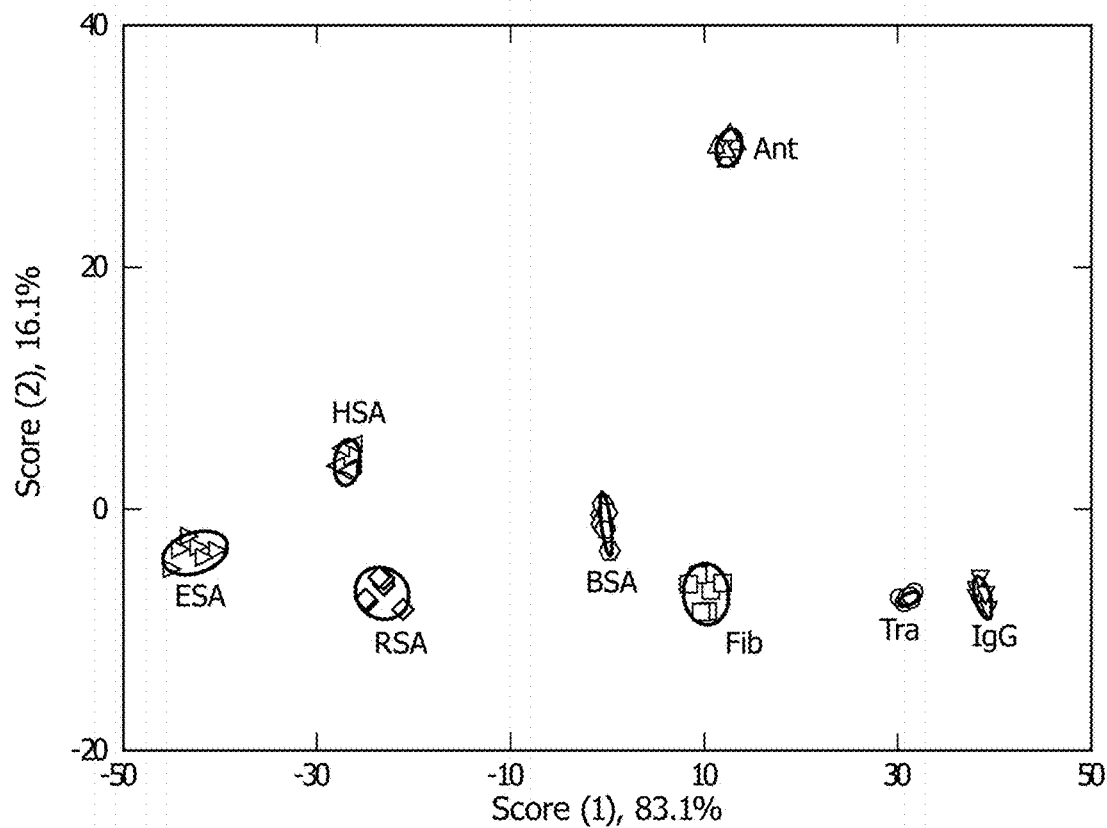
FIG. 15 is a graph obtained by analyzing the results shown in FIG. 13 (solvent condition: pH 5.5) by linear discriminant analysis and plotting the resulting quadratic discriminant scores.
Figure 16:
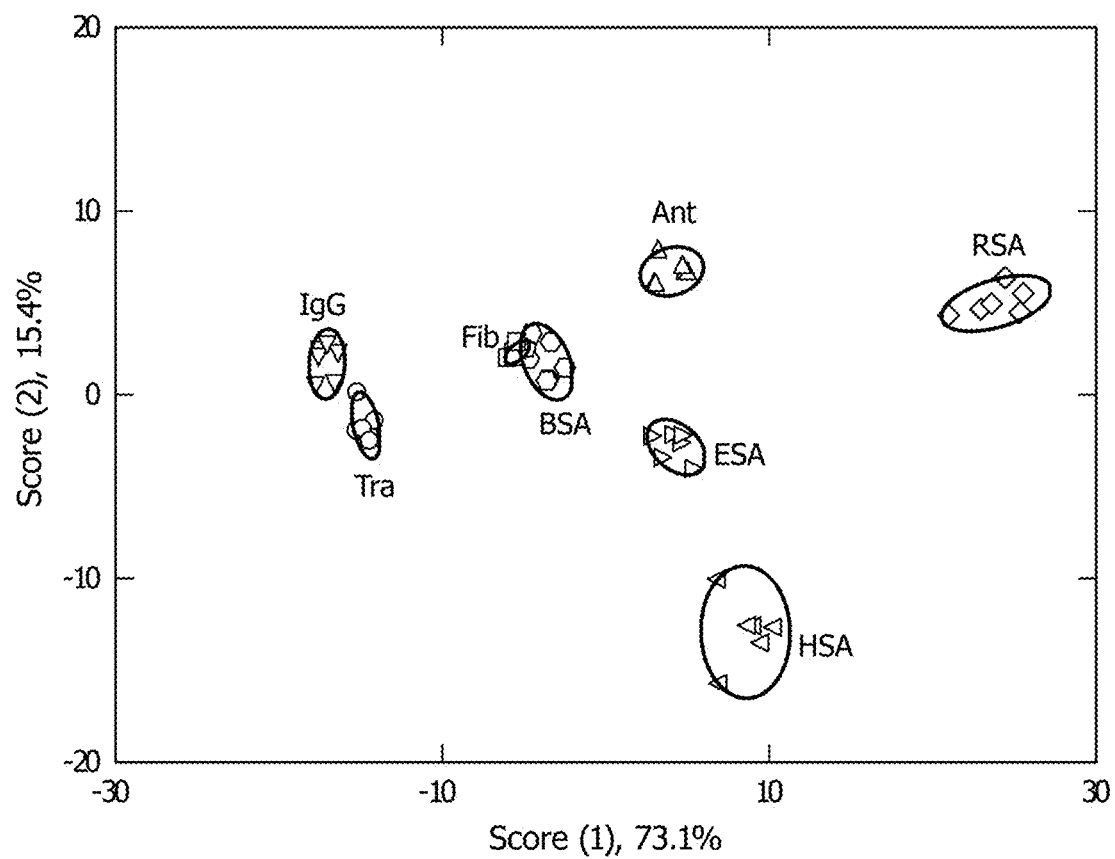
FIG. 16 is a graph obtained by analyzing the results shown in FIG. 13 (solvent condition: pH 8.5) by linear discriminant analysis and plotting the resulting quadratic discriminant scores.

FIGS. 15 and 16 show the results obtained by analyzing the results of measurement for each of the solvent conditions of pH 5.5 and pH 8.5 by linear discriminant analysis, and plotting the resulting quadratic discriminant scores. In the results of measurement obtained at the solvent condition of pH 5.5, the respective clusters of the proteins were distributed without overlapping, and each protein was able to be discriminated also by a jackknife method with an accuracy of 100%. In contrast, in the results of measurement obtained at the solvent condition of pH 8.5, the cluster of Fib and the cluster of BSA were not completely separated, but each protein was able to be discriminated in the analysis by a jackknife method with an accuracy of 100%.

Figure 17:
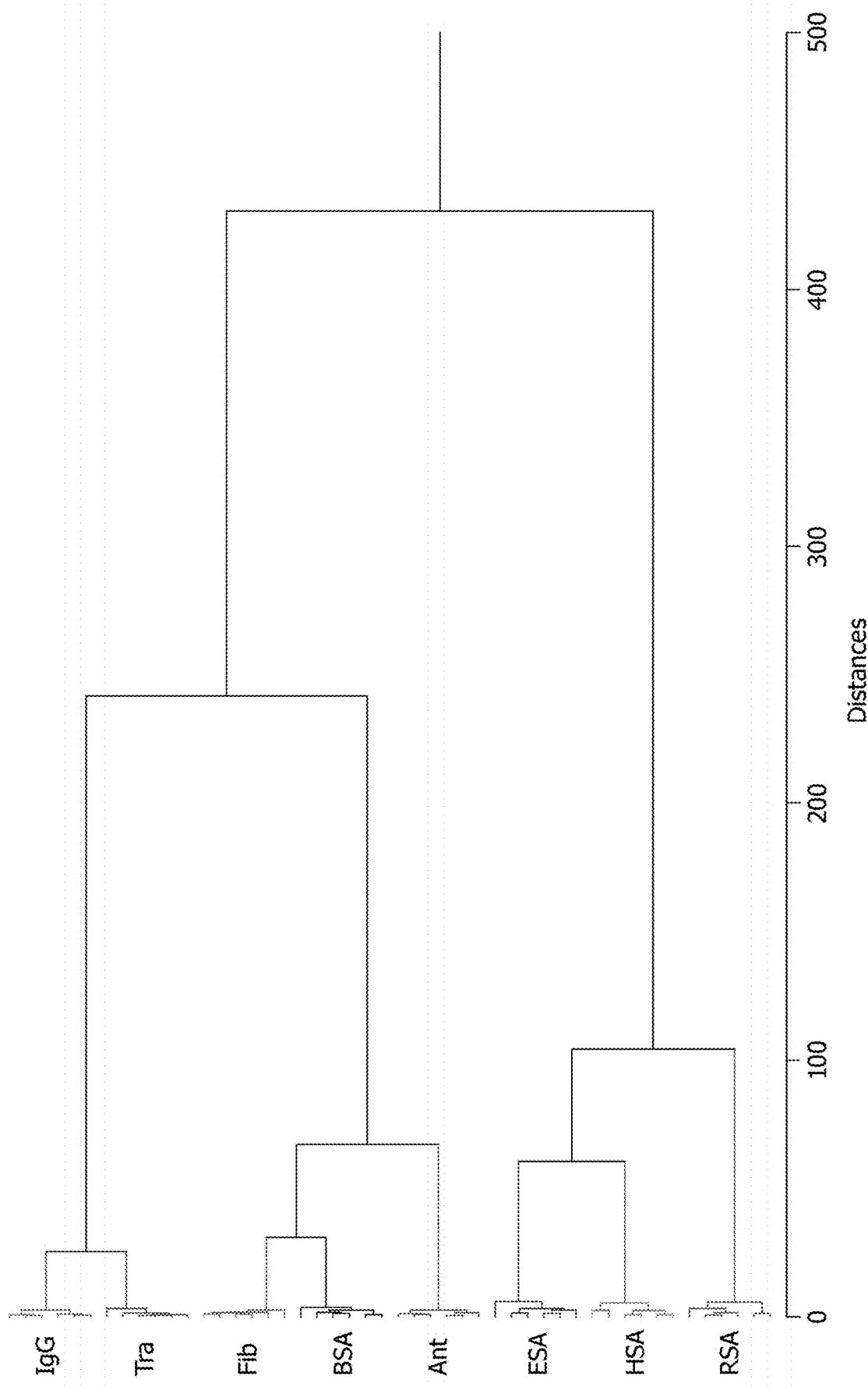
FIG. 17 is a dendrogram obtained by analyzing the results shown in FIG. 13 by hierarchical clustering analysis.

Furthermore, FIG. 17 shows the results of hierarchical clustering analysis of the measurement results shown in FIG. 13 (two solvent conditions×five probes) by a Ward's method. It was demonstrated that each protein can be clustered extremely well.

The above results demonstrated that all probes of Compounds 1 to 7 can well discriminate different proteins.

4. Discrimination of Identical Proteins Having Different Post-Translational Modifications It was tested whether the type and/or the presence or absence of a post-translational modification in identical proteins can be discriminated using PLL-Dnc (Compound 1).

(4-1) Discrimination of Presence or Absence of Post-Translational Modification in Albumin Fluorescent fingerprints of albumins shown in Table 1 and albumins having post-translational modifications shown in Table 2 were obtained as in the above (3-1) and were analyzed by linear discriminant analysis and hierarchical clustering analysis by a Ward's method.

TABLE 2

Albumin having post-translational modification

| Origin | Post-translational modification | Modified residue | Abbreviation |
| --- | --- | --- | --- |
| Bovine serum | Phosphorylation | Ser | BSA-PS |
| Bovine serum | Phosphorylation | Tyr | BSA-PY |
| Bovine serum | Acetylation | Lys | BSA-Ac |
| Bovine serum | Methylation | Glu, Asp | BSA-Me |
| Bovine serum | Saccharification (lactose) | Lys | BSA-Lac |
| Human serum | Saccharification (glucose) | Lys | HSA-Glc |

Figure 18:
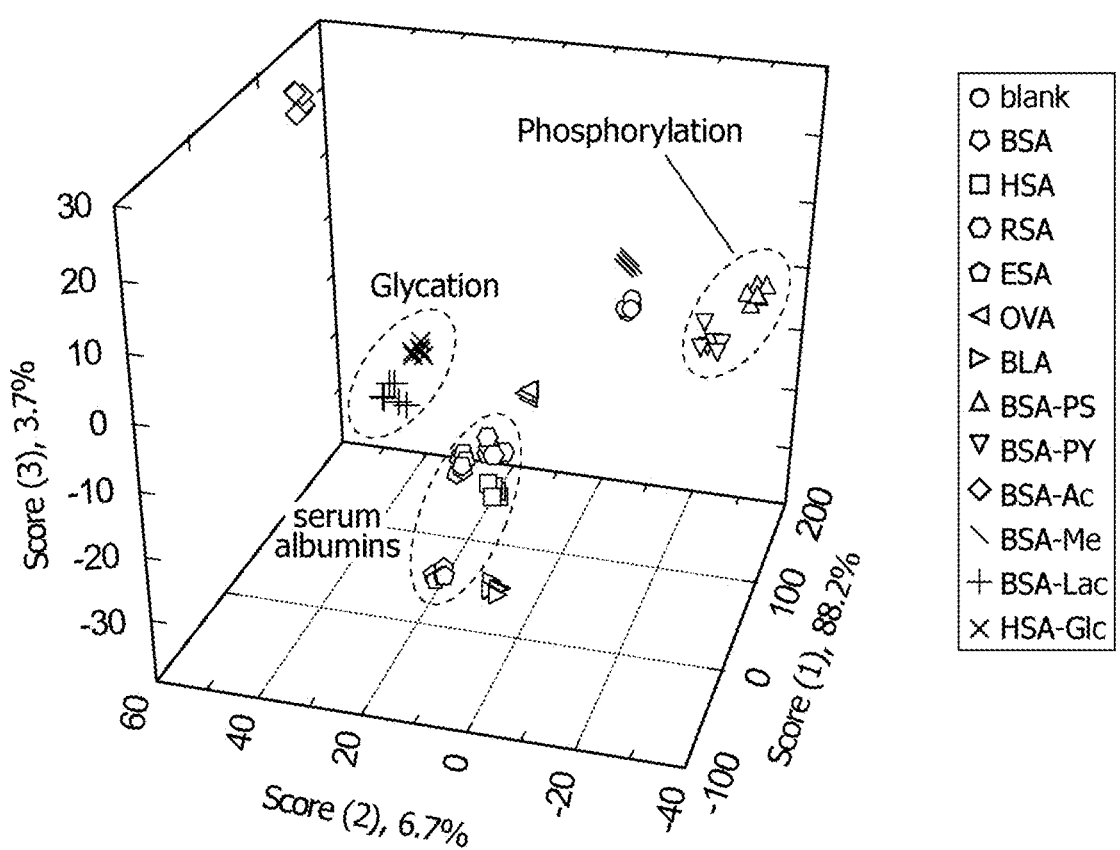
FIG. 18 is a graph obtained by analyzing, by linear discriminant analysis, the fluorescent fingerprints of various albumins with/without post-translational modifications obtained by using probe solutions prepared by dissolving PLL-Dnc (Compound 1) in six types of solvents and plotting the resulting cubic discriminant scores.
Figure 19:
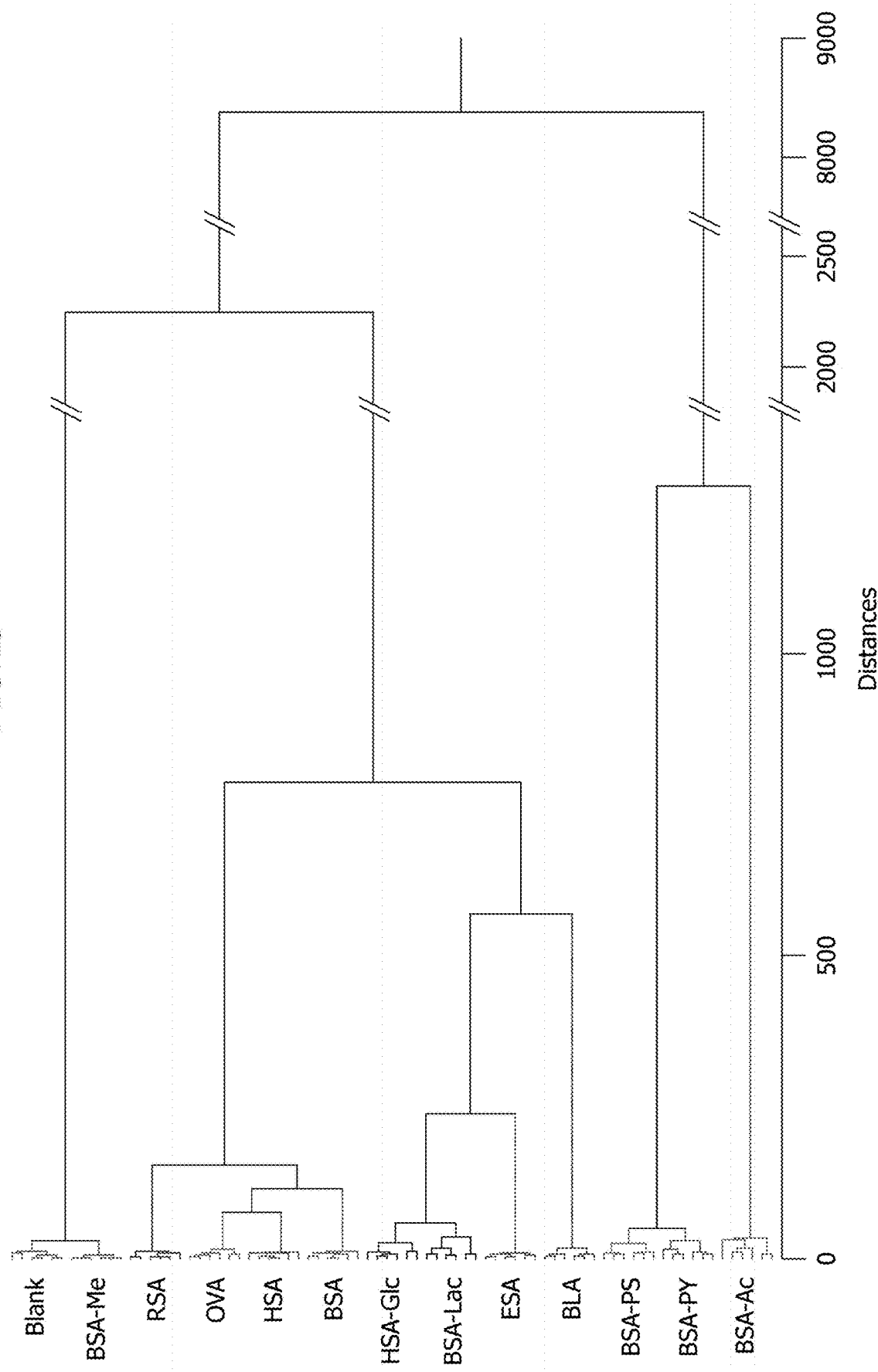
FIG. 19 is a dendrogram obtained by analyzing, by hierarchical clustering analysis, the fluorescent fingerprints of various albumins with/without post-translational modifications obtained by using probe solutions prepared by dissolving PLL-Dnc (Compound 1) in six types of solvents.

FIG. 18 shows the results of the linear discriminant analysis, and the FIG. 19 shows the results of the hierarchical clustering analysis. The results demonstrated that the presence or absence and the type of various post-translational modifications in identical proteins can be discriminated by PLL-Dnc (Compound 1).

(4-2) Quantification of Albumin into which Post-Translational Modification was Introduced Fluorescent fingerprints of a mixture of HSA and HSA-Glc (concentration: 0 to 30 μg/mL) and a mixture of BSA and BSA-PS (concentration: 0 to 9 μg/mL) were obtained as in the above (3-1) and were analyzed by linear discriminant analysis.

Figure 20A:
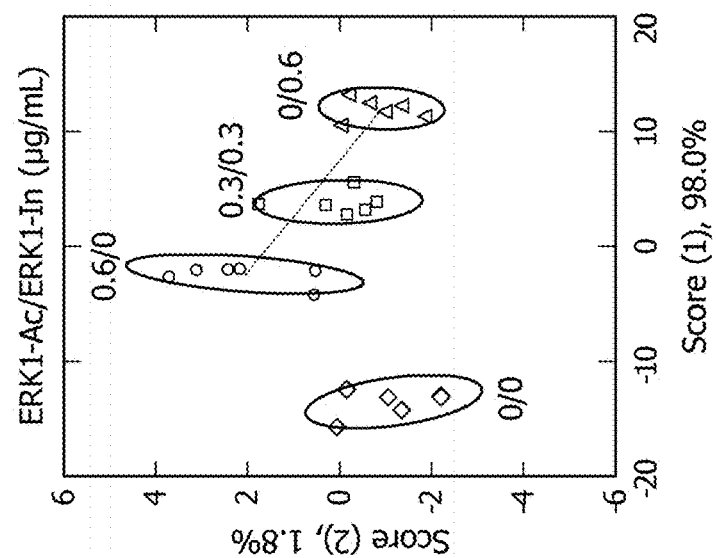
FIG. 20 shows graphs obtained by analyzing, by linear discriminant analysis, the fluorescent fingerprints of mixtures of proteins with/without post-translational modifications obtained by using probe solutions prepared by dissolving PLL-Dnc (Compound 1) in six types of solvents and plotting the resulting quadratic discriminant scores.
Figure 20B:
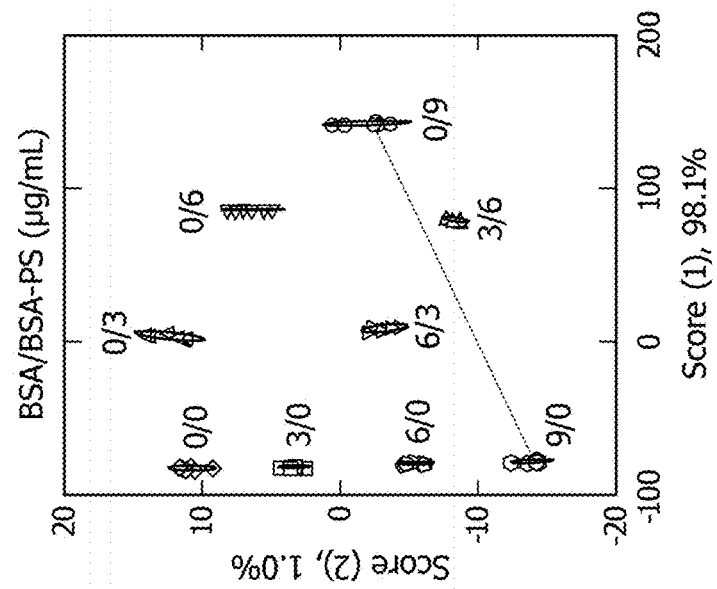
Figure 20C:
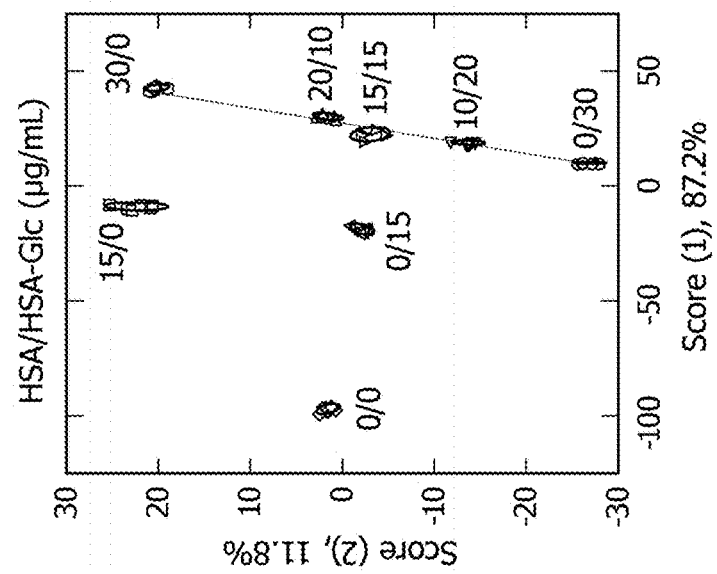

FIG. 20 (a) shows the results of analysis for the mixture of HSA and HSA-Glc, and FIG. 20 (b) shows the results of analysis for the mixture of BSA and BSA-PS. The presence or absence of a post-translational modification was able to be well discriminated even at a low concentration of 15 μg/mL (about 250 nM) in the mixture of HSA and HSA-Glc and a low concentration of 3 μg/mL (about 50 nM) in the mixture of BSA and BSA-PS. In addition, in both cases, all samples with different concentrations were able to be well discriminated.

(4-3) Quantification of Active/Inactive Extracellular Signal-Regulated Kinase (ERK1)

A fluorescent fingerprint of a mixture of inactive ERK1 without a post-translational modification (ERK1-in) and active ERK1 phosphorylated at T202 and Y204 (ERK1-ac) (concentration: 0 to 0.6 μg/mL) was obtained by the same procedure as in the above (3-1) except that the concentration of the probe solution was 1 μg/mL and was analyzed by linear discriminant analysis.

The results are shown in FIG. 20 (c). Active ERK1 and inactive ERK1 were well discriminated even at a low concentration (0.6 μg/mL, about 8 nM), and the concentration difference was also clearly discriminated. The above results demonstrated that PLL-Dnc (Compound 1) can not only discriminate the presence or absence of a post-translational modification, but can also measure the amount of the post-translational modification with high sensitivity.

Thus, it was demonstrated that only one or a few of the probes prepared by introducing an environment-sensitive fluorophore having a naphthalenesulfonic acid structure or a benzofurazan structure into a cationic polymer having a primary amino group, dissolved in a plurality of solvents having different ionic strengths and/or pH levels, can discriminate and quantify a wide variety of post-translational modifications with high sensitivity and high accuracy. It was confirmed that such a probe is useful for analyzing post-translational modifications.

5. Discrimination of Protein Component in Culture Medium Changed by Cultured Cells (5-1) Detection of Change in Protein Component in Culture Medium by Human Alveolar Basal Epithelial Cells (A549)

A549 cells (obtained from the JCRB cell bank) were suspended at a concentration of $1.2 \times 10^5$ cells/mL in D-MEM (containing high glucose, L-glutamine, and phenol red) (Wako Pure Chemical Industries, Ltd.) supplemented with 10% FBS (GE Life Science) and 1% penicillin streptomycin neomycin antibiotic mixture (PSN) (Life Technologies), and 500 μL of the suspension was placed in each well of a 24-well plate (AGC Techno Glass Co., Ltd.). The cells were cultured for 48 hours at 37° C. in a 5% $CO_2$ atmosphere. After removal of the medium, the cells were washed twice with 200 μL of phosphate buffered saline (PBS) (Wako Pure Chemical Industries, Ltd.), and 300 μL of 1×CD CHO Medium (Thermo Fisher Scientific) containing 1% FBS was added to each well. The cells were then cultured for 16 to 48 hours at 37° C. in a 5% $CO_2$ atmosphere. The culture medium was collected and was subjected to centrifugation at 3000 g for 10 minutes to collect the culture supernatant. Separately, a culture medium prepared by incubation under the same conditions as above without adding the cells was used as a control.

Five probes, Compounds 3 to 7 (P1 to P5), were each dissolved in 20 mM MOPS (pH 7.4) to prepare probe solutions (2.1 μg/mL). Each probe solution was dispensed in a 96-well microplate (Corning, Inc.) at 190 μL/well, and 10 μL of the culture supernatant obtained above was added to each well, followed by mixing. After incubation at 30° C. for 10 minutes, the fluorescence intensities were measured at the following two sets of excitation wavelength (nm)/emission wavelength (nm): (Ch1) 320/560 and (Ch2) 340/480. The measurement was repeated six times for each probe.

Figure 22:
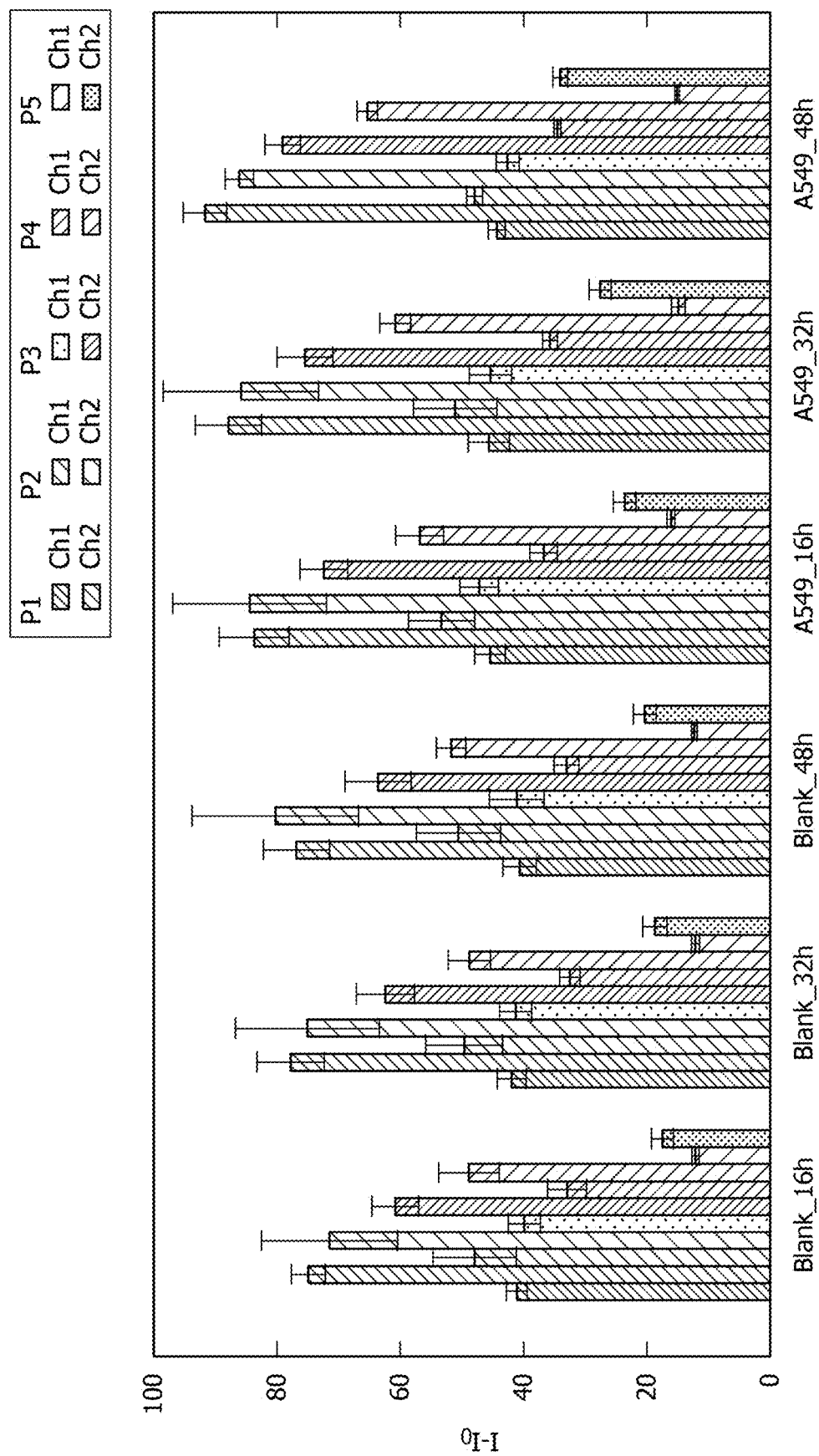
FIG. 22 is a graph showing the amounts of change in fluorescence intensity when supernatants of A549 cells cultured at different culture times were each added to five types of probe solutions (Compounds 3 to 7: P1 to P5/20 mM MOPS (pH 7.4)).
Figure 23:
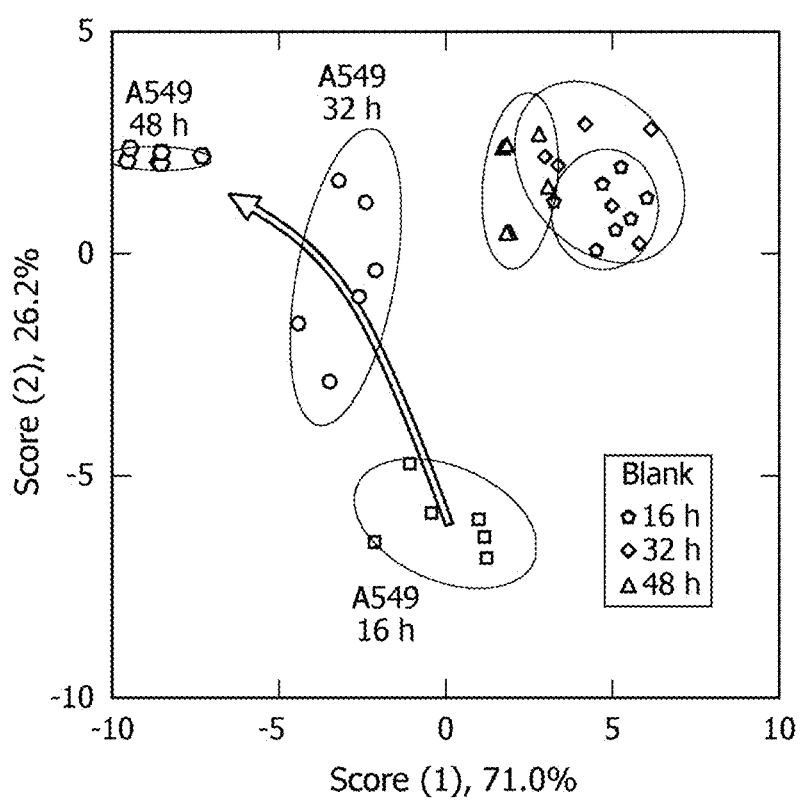
FIG. 23 is a graph obtained by analyzing the results shown in FIG. 22 by linear discriminant analysis and plotting the resulting quadratic discriminant scores.

The results of measurement (two sets of wavelengths×five probes) are shown in FIG. 22. The vertical axis ($I-I_0$) represents the amount of change in the fluorescence intensity by adding a sample (culture medium or culture supernatant). FIG. 23 shows the results obtained by analyzing the measurement results by linear discriminant analysis and plotting the resulting quadratic discriminant scores. Whereas the fluorescent fingerprint of the culture medium (Blank) did not change with time, the fluorescent fingerprint of the culture supernatant of A549 cells changed with the culture time so as to give unique fluorescent fingerprints that varied according to the culture time.

(5-2) Discrimination of Type of Cells Based on Change in Protein Component in Culture Medium Culture supernatants of A549 cells, human liver cancer cells (HepG2) (obtained from the JCRB cell bank), human osteosarcoma cells (MG63) (obtained from the JCRB cell bank), and human bone marrow-derived mesenchymal stem cells (UE7T-13) (obtained from the JCRB cell bank) were collected after culturing for 48 hours by the same procedure as in the above (5-1), and the fluorescent fingerprints (two sets of wavelengths×five probes) of the culture supernatants were obtained, and the resulting fluorescent fingerprints were analyzed by linear discriminant analysis. Separately, a culture medium prepared by incubation under the same conditions as above without adding the cells was used as a control.

Figure 24:
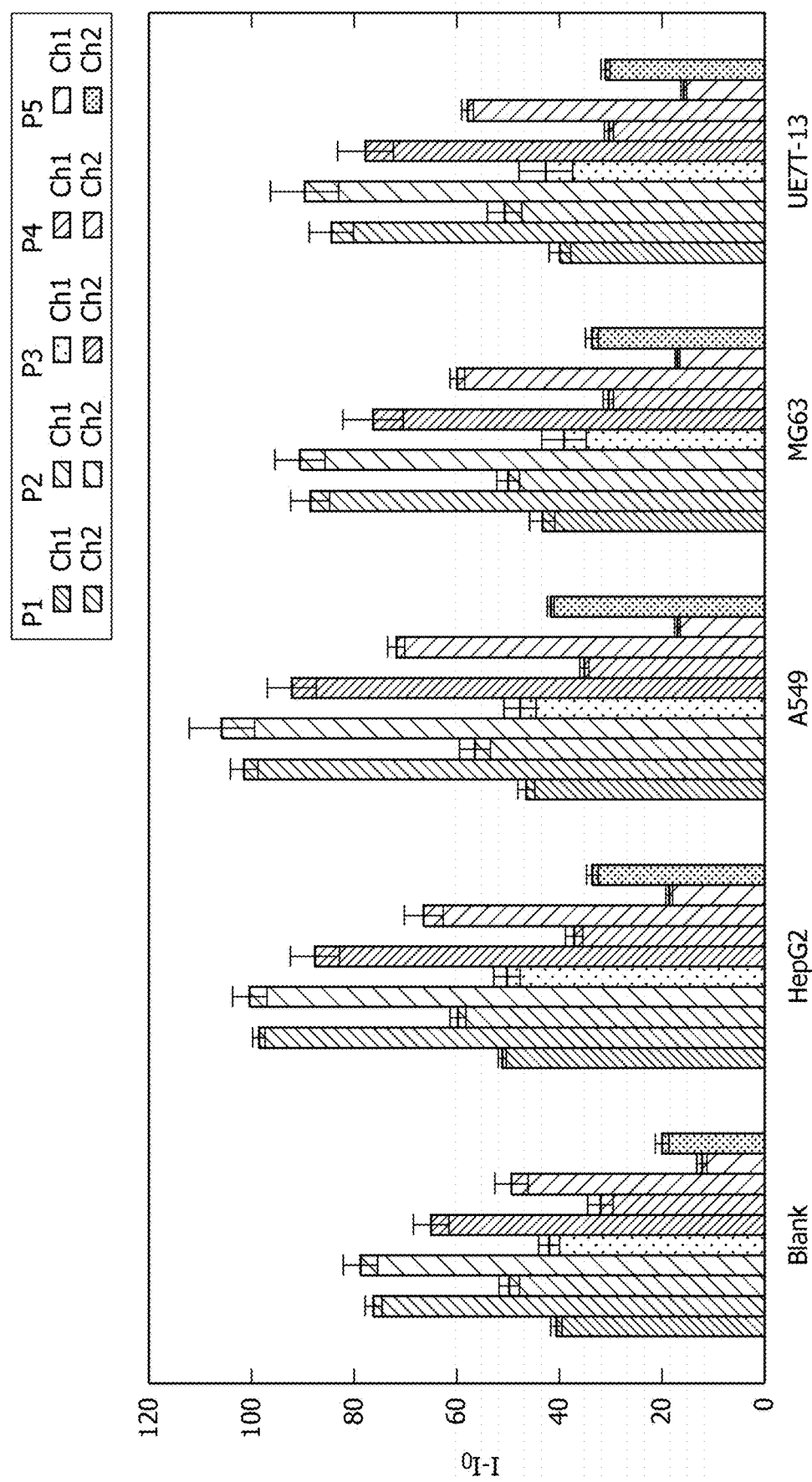
FIG. 24 is a graph showing the amounts of change in fluorescence intensity when culture supernatants of four types of cells were each added to five types of probe solutions (Compounds 3 to 7: P1 to P5/20 mM MOPS (pH 7.4)).
Figure 25:
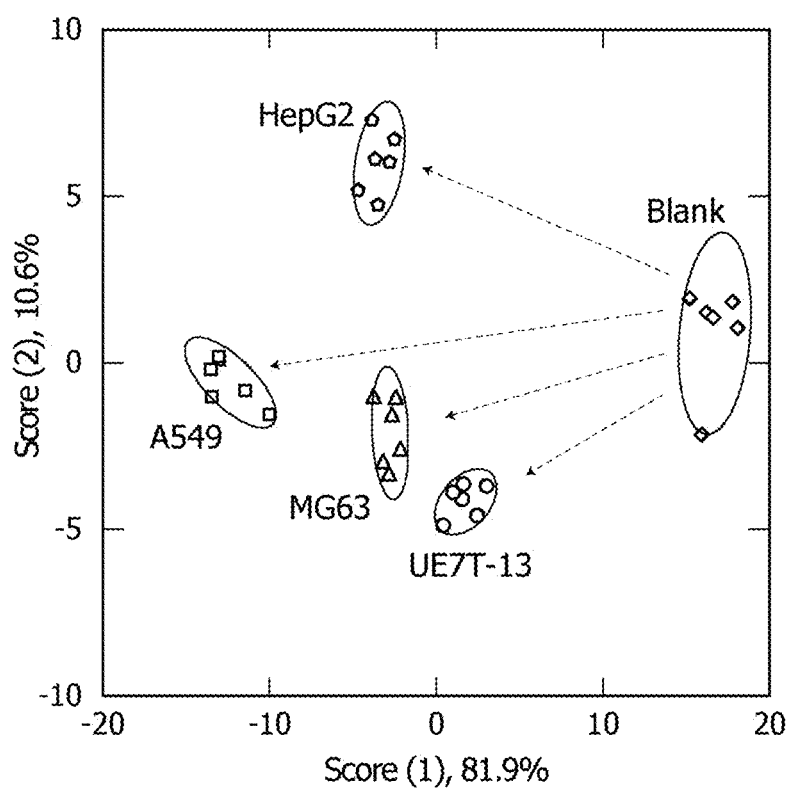
FIG. 25 is a graph obtained by analyzing the results shown in FIG. 24 by linear discriminant analysis and plotting the resulting quadratic discriminant scores.

FIG. 24 shows the resulting fluorescent fingerprints, and FIG. 25 shows the results of linear discriminant analysis. The respective clusters of the cells were distributed without overlapping. The results were further analyzed by a jackknife method to verify that each cell can be discriminated with an accuracy of 100%. In addition, each cell was able to be discriminated with an accuracy of 90% also by a blind test based on the Mahalanobis distance. The above results demonstrated that the type of cells can be discriminated by analyzing cell culture supernatant with probes of Compounds 3 to 7 (P1 to P5).

(5-3) Discrimination of Concentration of Cells Based on Change in Protein Component in Culture Medium The culture supernatants of A549 cells at concentrations of 0, $0.4\times10^5$, $0.8\times10^5$, and $1.2\times10^5$ cells/mL were collected after culturing for 48 hours by the same procedure as in the above (5-1). The fluorescent fingerprints (two sets of wavelengths×five probes) of the culture supernatants were obtained. The resulting fluorescent fingerprints (two sets of wavelengths×two probes (Compounds 3 and 4)) were further analyzed by linear discriminant analysis.

Figure 26:
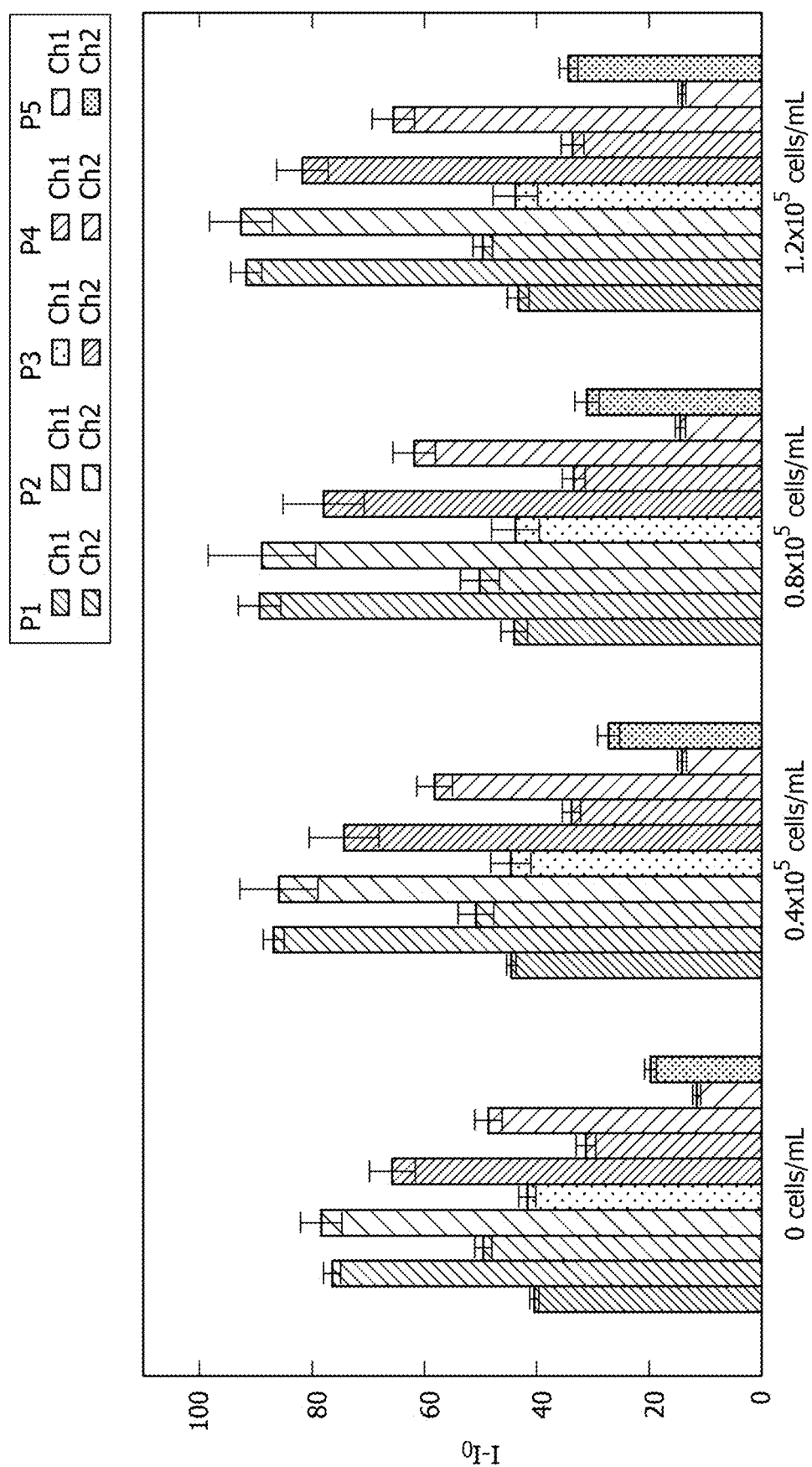
FIG. 26 is a graph showing the amounts of change in fluorescence intensity when supernatants of A549 cells cultured at different cell concentrations were each added to five types of probe solutions (Compounds 3 to 7: P1 to P5/20 mM MOPS (pH 7.4)).
Figure 27A:
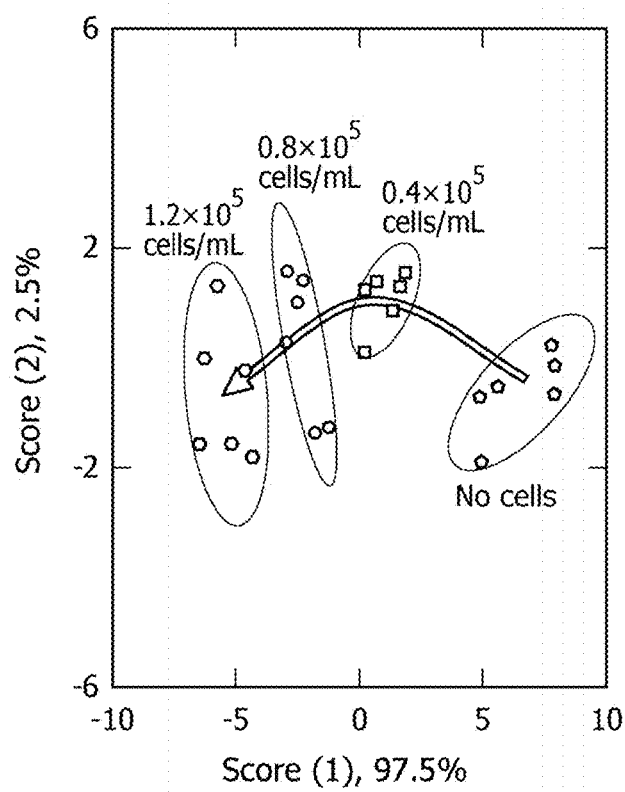
FIG. 27 shows graphs obtained by analyzing the results shown in FIG. 26 by linear discriminant analysis and plotting the resulting quadratic discriminant scores (a) and plotting the cell concentrations with respect to the resulting linear discriminant scores (b).
Figure 27B:
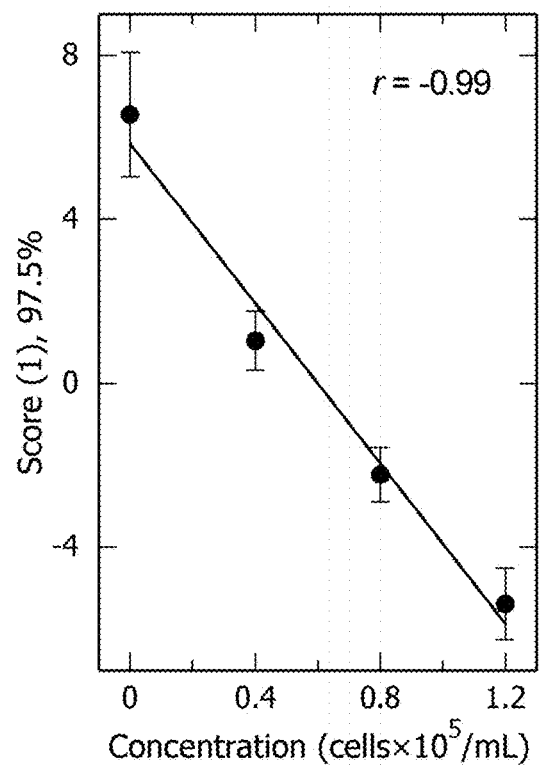

FIG. 26 shows the resulting fluorescent fingerprints, and FIG. 27 shows the results of linear discriminant analysis. The respective clusters of the cells at each concentration were distributed without overlapping (FIG. 27 (a)). The results were further analyzed by a jackknife method to verify that each cell concentration can be discriminated with an accuracy of 100%. In addition, each cell concentration was able to be discriminated with an accuracy of 88% also by a blind test based on the Mahalanobis distance. The linear discriminant scores obtained by the linear discriminant analysis were plotted with respect to the cell concentration, and as a result, a high linear correlation was observed between the linear discriminant score and the cell concentration ($r=-0.99$) (FIG. 27 (b)). The above results demonstrated that cell concentrations can be quantified by analyzing the cell culture supernatants with the probes of Compounds 3 to 7 (P1 to P5).

(5-4) Discrimination of Mixture Ratio of a Plurality of Types of Cells Based on Change in Protein Component in Culture Medium The culture supernatants of cultured mixtures of HepG2 and UE7T-13 cells (total concentration: $1.2\times10^5$ cells/mL) were collected after culturing for 48 hours by the same procedure as in the above (5-1). The fluorescent fingerprints (two sets of wavelengths×five probes) of the culture supernatants were obtained. The resulting fluorescent fingerprints (two sets of wavelengths (only Ch1 for Compounds 3, 5, and 7)×five probes) were further analyzed by linear discriminant analysis.

Figure 28:
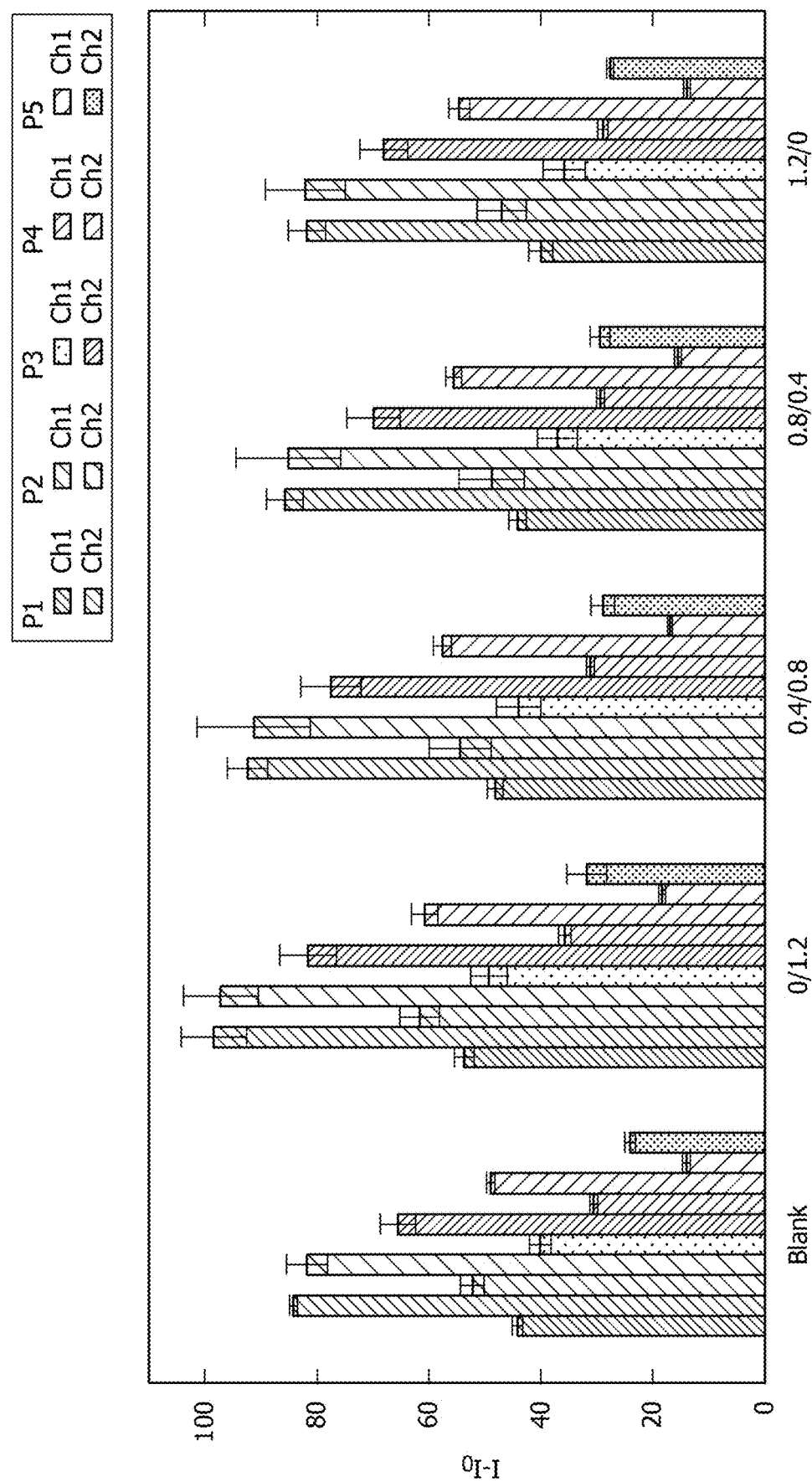
FIG. 28 is a graph showing the amounts of change in fluorescence intensity when supernatants of culture of HepG2 cells and UE7T-13 cells mixed at different ratios were each added to five types of probe solutions (Compounds 3 to 7: P1 to P5/20 mM MOPS (pH 7.4)).

FIG. 28 shows the resulting fluorescent fingerprints, and FIG. 29 shows the results of linear discriminant analysis. The respective clusters of the cultured mixtures were distributed without overlapping (FIG. 29 (a)). The results were further analyzed by a jackknife method to verify that each cultured mixture can be discriminated with an accuracy of 97%. In addition, each cultured mixture was able to be discriminated with an accuracy of 95% also by a blind test based on the Mahalanobis distance. The linear discriminant scores obtained by the linear discriminant analysis were plotted with respect to the ratio of HepG2 cells in the cultured mixture. The result showed a high linear correlation between the linear discriminant score and the ratio of HepG2 cells in the cultured mixture ($r=0.99$) (FIG. 29 (b)). The above results demonstrated that mixture ratio of cells in a cultured mixture of a plurality of types of cells can be quantified by analyzing the cell culture supernatants with the probes of Compounds 3 to 7 (P1 to P5).

(5-5) Discrimination of Degree of Cell Differentiation Based on Change in Protein Component in Culture Medium Human bone marrow-derived mesenchymal stem cells UE7T-13 were induced to differentiate into osteoblasts by the following procedure. As in the above (5-1), UE7T-13 cells were suspended at a concentration of $1.2\times10^5$ cells/mL in D-MEM supplemented with 10% FBS and 1% PSN, and 400 µL of the suspension was placed in each well of a 24-well plate. The cells were cultured for 24 hours at 37° C. in a 5% $CO_2$ atmosphere and allowed to adhere. The culture medium was removed and replaced with 400 µL of a fresh D-MEM mentioned above. After culturing for further 24 hours, the culture medium was removed and replaced with a differentiation induction medium (D-MEM (10% FBS, 1% PSN) supplemented with 0.1 µM dexamethasone (Sigma-Aldrich), 10 mM P3-glycerophosphoric acid (Sigma-Aldrich), and 0.2 mM ascorbic acid (Sigma-Aldrich)) so as to induce differentiation. The medium was replaced with a fresh differentiation induction medium every 72 hours. The culture supernatants were collected at 0 hours (first day of differentiation induction), 72 hours (4th day), 168 hours (8th day), and 264 hours (12th day) after the start of induction, and the fluorescent fingerprints (two sets of wavelengths× five probes, probe solvent: 20 mM MES (pH 5.4)) of the culture supernatants were obtained, as in above (5-1). The resulting fluorescent fingerprints (two sets of wavelengths× four probes (Compounds 3 and 5 to 7)) were analyzed by linear discriminant analysis. Separately, a culture supernatant collected from culture without inducing differentiation using D-MEM (10% FBS, 1% PSN) instead of the differentiation induction medium was used as a control.

Figure 30:
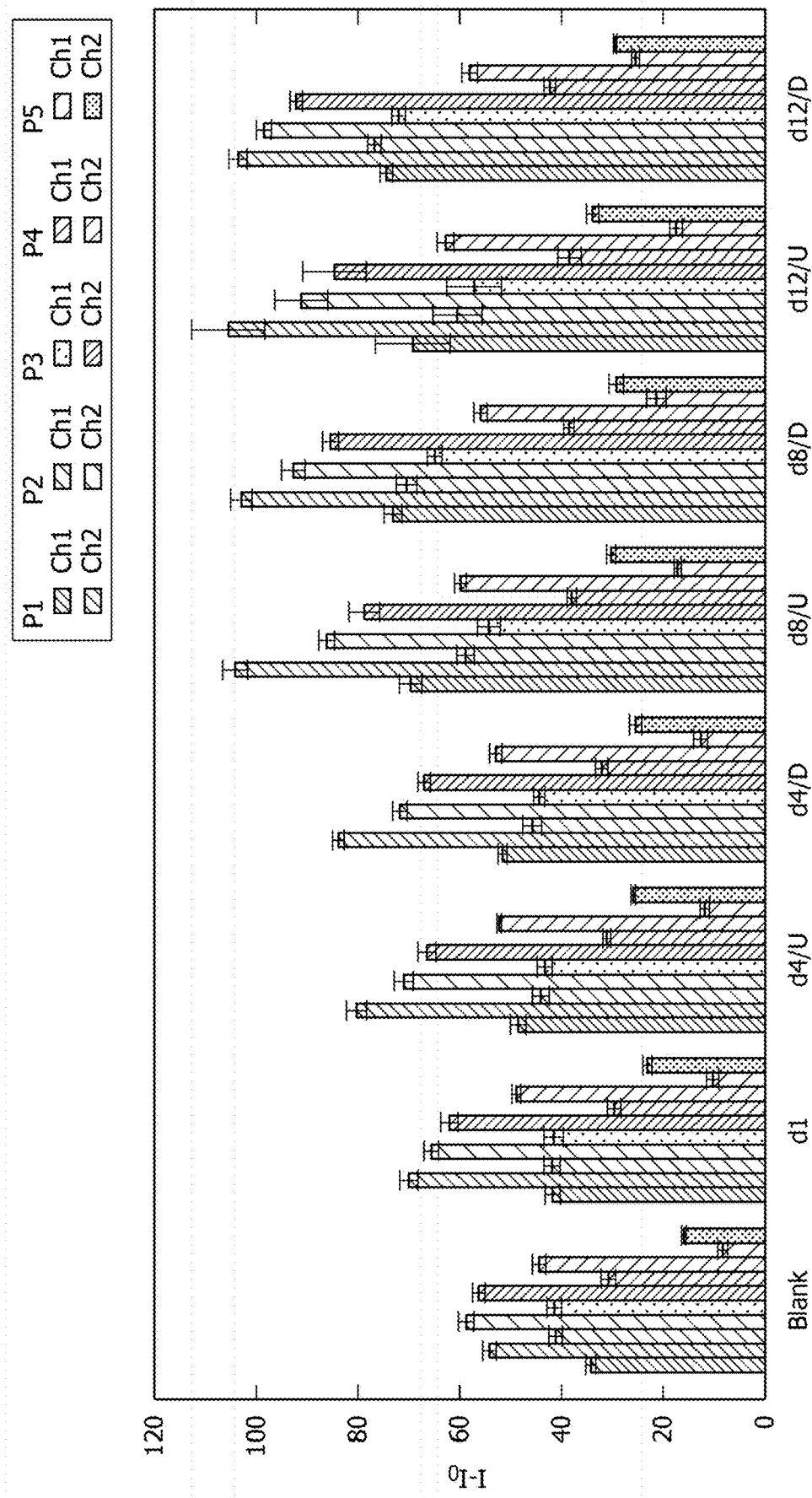
FIG. 30 is a graph showing the amounts of change in fluorescence intensity when supernatants of UE7T-13 cells cultured with/without induction of differentiation were added to five types of probe solutions (Compounds 3 to 7: P1 to P5/20 mM MES (pH 5.4)).
Figure 31:
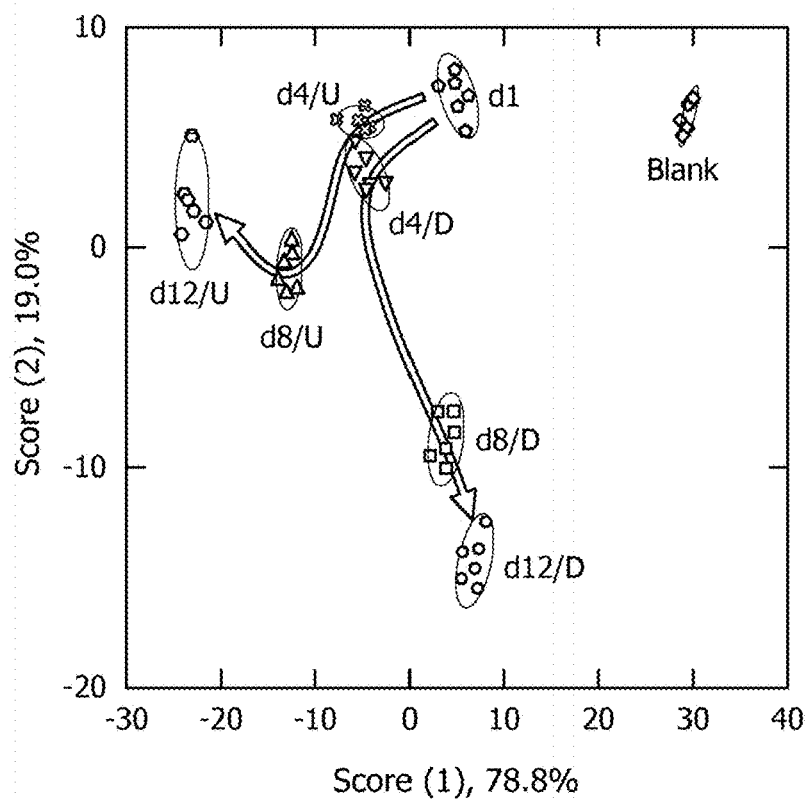
FIG. 31 is a graph obtained by analyzing the results shown in FIG. 30 by linear discriminant analysis and plotting the resulting quadratic discriminant scores.

FIG. 30 shows the resulting fluorescent fingerprints, and FIG. 31 shows the results of linear discriminant analysis. In the Figures, "d" represents the number of days of culture after the start of differentiation induction, "D" indicates culture with inducing differentiation, and "U" indicates culture without inducing differentiation. At 72 hours after the start of induction, the clusters of the culture with inducing differentiation and the culture without inducing differentiation were distributed without overlapping (FIG. 31, d4/D, d4/U). The results were further analyzed by a jackknife method to verify that each cell can be discriminated at each culture condition and time with an accuracy of 100%. In addition, each cell was able to be discriminated at each culture condition and time with an accuracy of 97% also by a blind test based on the Mahalanobis distance.

The degrees of differentiation of the culture with inducing differentiation and the culture without inducing differentiation of UE7T-13 cells prepared as above were evaluated by Alizarin Red S staining. The Alizarin Red S staining detects calcification occurring as a result of differentiation of UE7T-13 cells into osteoblast. The Alizarin Red S staining was performed by the following procedure. The culture medium was removed from the cultures after 72 hours, 168 hours, and 264 hours from the start of induction. After washing twice with 200 µL of PBS, 200 µL of 4% paraformaldehyde (4° C.) was added to each culture, followed by incubation at 37° C. in a 5% $CO_2$ atmosphere for 15 minutes. After washing with 300 µL of sterilized water three times, 300 µL of methanol (−20° C.) was added thereto, followed by incubation at 37° C. in a 5% $CO_2$ atmosphere for 10 minutes. After washing once with 200 µL of sterilized water, 200 µL of an aqueous solution of 0.1 mg/mL of Alizarin Red S (Sigma-Aldrich) (adjusted to pH 6.4 with KOH aqueous solution) was added thereto, followed by incubation at 37° C. in a 5% $CO_2$ atmosphere for 15 minutes. After washing twice with 200 µL of sterilized water, 100 µL of sterilized water was added thereto, followed by observation under a bright-field microscope.

Figure 32:
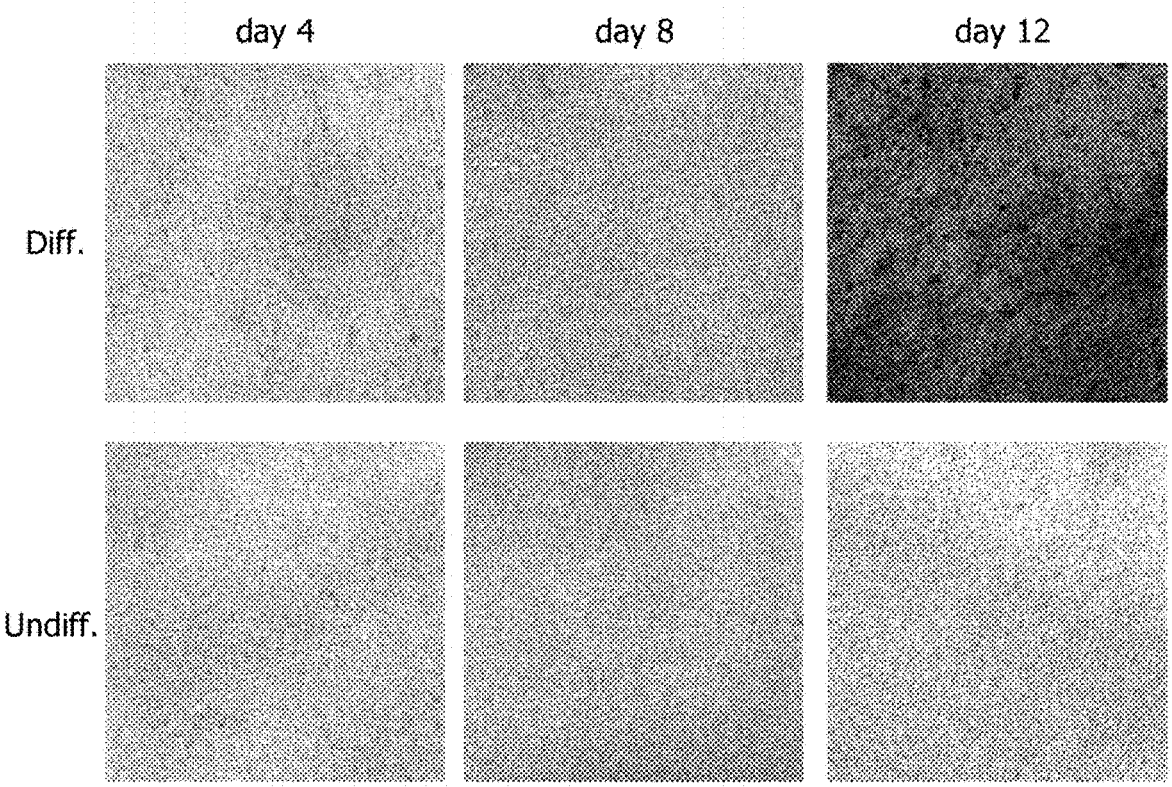
FIG. 32 shows bright-field microscopic images of UE7T-13 cells with/without differentiation induction stained with Alizarin Red S.

FIG. 32 shows the results. Calcification was not detected on the 4th day and 8th day of induction, and calcification was first detected on the 12th day of induction. The above results demonstrated that analysis of a cell culture supernatant with probes of Compounds 3 to 7 (P1 to P5) can detect the differentiation state in the early stage that cannot be detected by Alizarin Red S staining and can discriminate a slight difference in the degree of differentiation.

The invention claimed is:

1. A method for analyzing a protein-containing sample, comprising:
   (1) dissolving a probe capable of non-specifically interacting with a plurality of proteins in a plurality of solvents having different ionic strengths and/or pH levels,
   wherein the probe comprises:
      (a) a cationic polymer comprising at least five primary amino groups in one molecule and having a weight-average molecular weight of 1,000 to 500,000; and
      (b) an environment-sensitive fluorophore having a naphthalenesulfonic acid structure or a benzofurazan structure, and
   wherein the fluorophore is covalently bonded to some of the primary amino groups in the cationic polymer;
   (2) adding a test sample containing one or more proteins to a plurality of probe solutions prepared in the step (1), thereby the proteins in the test sample and the probe are interacted non-specifically;
   (3) measuring fluorescence intensities of the plurality of probe solutions to which the test sample has been added in the step (2); and
   (4) comparing the pattern of fluorescence intensities obtained in the step (3) with the pattern of fluorescence intensities obtained from a reference sample.

2. The method according to claim 1, wherein the environment-sensitive fluorophore is selected from the group consisting of dansyl, dimethylaminosulfonyl benzoxadiazole, and fluorescent derivatives thereof.

3. The method according to claim 1, wherein the cationic polymer is a linear or branched polyamino acid, polyallylamine, polyamidoamine, or polyalkyleneimine.

4. The method according to claim 3, wherein the polyamino acid is polylysine or polyornithine.

5. The method according to claim 1, wherein the environment-sensitive fluorophore is covalently bonded to 1% to 50% of the primary amino groups in the cationic polymer.

6. The method according to claim 1, wherein a functional group selected from the group consisting of a guanidium group, an alkyl group, an aryl group, a carboxyl group, and an amino acid is introduced into at least some of the primary amino groups not covalently bonded to the environment-sensitive fluorophore in the cationic polymer.

7. The method according to claim 1, wherein the measurement of the fluorescence intensities in the step (3) is performed at a plurality of excitation wavelengths and emission wavelengths.

8. The method according to claim 1, wherein the step (4) determines types and/or amounts of protein and post-translational modification thereto contained in the test sample.

9. The method according to claim 1, wherein the test sample is a cell culture supernatant, and the step (4) determines the type and/or state and/or concentration of cells being cultured.

10. The method according to claim 9, wherein the state of cells being cultured is a degree of cell differentiation.

11. The method according to claim 1, wherein the cationic polymer has a weight-average molecular weight of 1,500 to 200,000.

12. The method according to claim 1, wherein the cationic polymer has a weight-average molecular weight of 2,000 to 100,000.

* * * * *

UNITED STATES PATENT AND TRADEMARK OFFICE
CERTIFICATE OF CORRECTION

PATENT NO. : 11,397,185 B2
APPLICATION NO. : 16/348312
DATED : July 26, 2022
INVENTOR(S) : Tomita et al.

It is certified that error appears in the above-identified patent and that said Letters Patent is hereby corrected as shown below:

In the Specification

Column 14, Line 34: Please correct "5 g/mL" to read --5 µg/mL--

Column 20, Line 21: Please correct "P3-glycerophosphoric" to read --β-glycerophosphoric--

Signed and Sealed this
Eleventh Day of April, 2023

*Katherine Kelly Vidal*

Katherine Kelly Vidal
*Director of the United States Patent and Trademark Office*